United States Patent [19]
Grulke et al.

[11] Patent Number: 5,797,679
[45] Date of Patent: Aug. 25, 1998

[54] SURGICAL CEMENT MIXER APPARATUS

[75] Inventors: David H. Grulke, Battle Creek; Richard F. Huyser, Kalamazoo, both of Mich.; Eugene Lautenschlager, Skokie, Ill.; Dennis A. Stratton, Plainwell; Harry A. Wellons, III, Portage, both of Mich.; Richard L. Wixson, Chicago, Ill.

[73] Assignee: Stryker Corporation, Kalamazoo, Mich.

[21] Appl. No.: 650,383

[22] Filed: May 17, 1996

Related U.S. Application Data

[63] Continuation of Ser. No. 599,253, Feb. 9, 1996.

[51] Int. Cl.⁶ .......................... B01F 13/06; B01F 15/02; B01F 7/20
[52] U.S. Cl. .......................... 366/139; 366/244; 366/195; 366/256
[58] Field of Search .......................... 366/189, 242, 366/244, 255, 256, 139, 195, 196

[56] References Cited

U.S. PATENT DOCUMENTS

| D. 279,499 | 7/1985 | Case. |
|---|---|---|
| 414,566 | 11/1889 | Nelleson. |
| 740,751 | 10/1903 | Friedman. |
| 1,023,368 | 4/1912 | Fay. |
| 1,033,667 | 7/1912 | Brown. |
| 1,177,295 | 3/1916 | Beckner .................... 366/242 |
| 1,181,869 | 5/1916 | Gerbing. |
| 1,415,735 | 5/1922 | Trust et al.. |
| 2,095,543 | 10/1937 | Doll. |
| 2,157,217 | 5/1939 | Rauch. |
| 2,224,967 | 12/1940 | Kaye. |
| 2,347,195 | 4/1944 | Huff. |
| 2,570,079 | 10/1951 | Spremulli. |
| 2,696,022 | 12/1954 | Steinbock et al.. |
| 2,973,187 | 2/1961 | Wehmer. |
| 3,112,743 | 12/1963 | Cochran et al.. |
| 3,223,083 | 12/1965 | Cobey. |
| 3,225,760 | 12/1965 | Di Cosola. |
| 3,255,747 | 6/1966 | Cochran et al.. |
| 3,290,017 | 12/1966 | Davies et al.. |
| 3,330,282 | 7/1967 | Visser et al.. |
| 3,342,460 | 9/1967 | Bolde. |
| 3,368,592 | 2/1968 | Thiel et al.. |
| 3,459,175 | 8/1969 | Miller. |
| 3,635,901 | 1/1972 | Urgesi et al.. |
| 3,739,947 | 6/1973 | Baumann et al.. |
| 3,815,878 | 6/1974 | Baskas et al.. |
| 3,907,106 | 9/1975 | Purrmann et al.. |
| 4,015,945 | 4/1977 | Frankel et al.. |
| 4,020,154 | 4/1977 | Perla et al.. |
| 4,185,072 | 1/1980 | Puderbaugh et al.. |
| 4,277,184 | 7/1981 | Solomon. |
| 4,380,399 | 4/1983 | Godat et al.. |
| 4,399,814 | 8/1983 | Pratt, Jr. et al.. |
| 4,438,074 | 3/1984 | Wilt. |
| 4,460,279 | 7/1984 | Krasney. |
| 4,462,694 | 7/1984 | Ernster et al.. |
| 4,488,817 | 12/1984 | Uesaka et al.. |

(List continued on next page.)

FOREIGN PATENT DOCUMENTS

| 1 163 504 | 2/1963 | Germany. | |
|---|---|---|---|
| 1 193 479 | 5/1965 | Germany .................... | 366/330 |
| 372 885 | 12/1963 | Switzerland. | |

*Primary Examiner*—Tony G. Soohoo
*Attorney, Agent, or Firm*—Flynn, Thiel, Boutell & Tanis, P.C.

[57] ABSTRACT

Apparatus for mixing a two part cement of a type adapted for fixing a repair element to hard, rigid tissue of a patient and containing the mixed cement preparatory to dispensing for such fixation. A mixing chamber has an outlet for mixed cement. A cartridge has an inlet releasably coupled to the outlet of the mixing chamber for receiving mixed cement therefrom. A rotating blade in the mixing chamber mixes cement, removes voids therefrom and moves mixed cement off the inner surface of the mixing chamber and into the cartridge.

39 Claims, 17 Drawing Sheets

U.S. PATENT DOCUMENTS

| | | |
|---|---|---|
| 4,515,267 | 5/1985 | Welsh . |
| 4,586,823 | 5/1986 | Schoendorfer et al. . |
| 4,671,263 | 6/1987 | Draenert . |
| 4,676,655 | 6/1987 | Handler . |
| 4,721,390 | 1/1988 | Lidgren . |
| 4,723,581 | 2/1988 | Staudenrausch et al. . |
| 4,758,096 | 7/1988 | Gunnarsson . |
| 4,787,751 | 11/1988 | Bakels . |
| 4,854,716 | 8/1989 | Ziemann et al. . |
| 4,961,647 | 10/1990 | Coutts et al. . |
| 4,966,601 | 10/1990 | Draenert . |
| 4,973,168 | 11/1990 | Chan . |
| 5,015,101 | 5/1991 | Draenert . |
| 5,265,956 | 11/1993 | Nelson et al. ............ 366/139 |
| 5,344,232 | 9/1994 | Nelson et al. ............ 366/139 |
| 5,415,474 | 5/1995 | Nelson et al. ............ 366/139 |
| 5,558,136 | 9/1996 | Orrico ............ 141/23 |

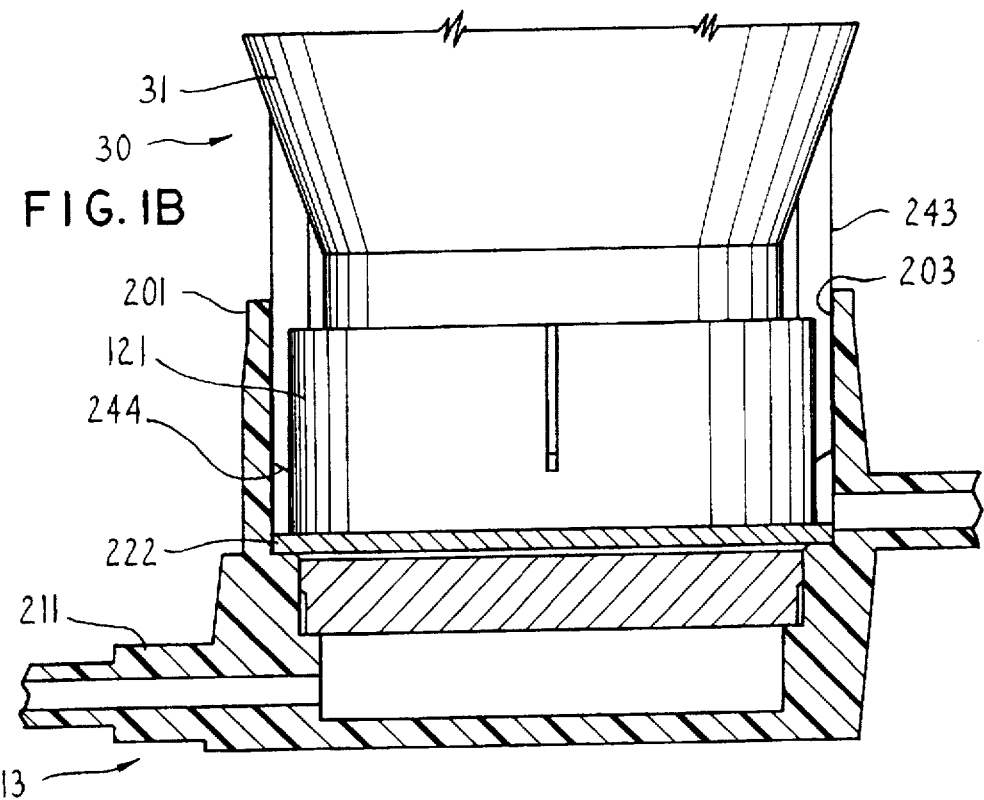
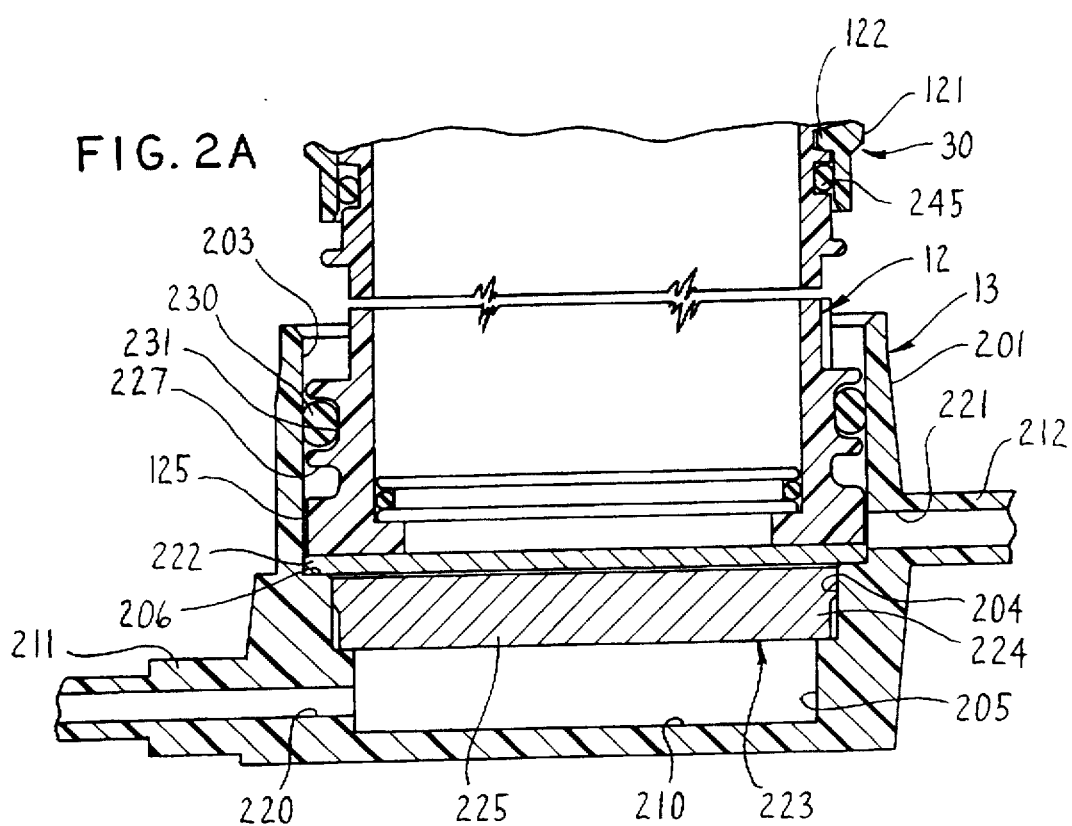

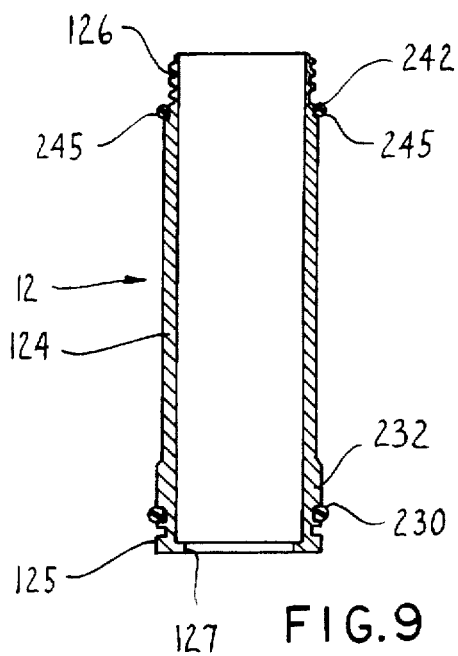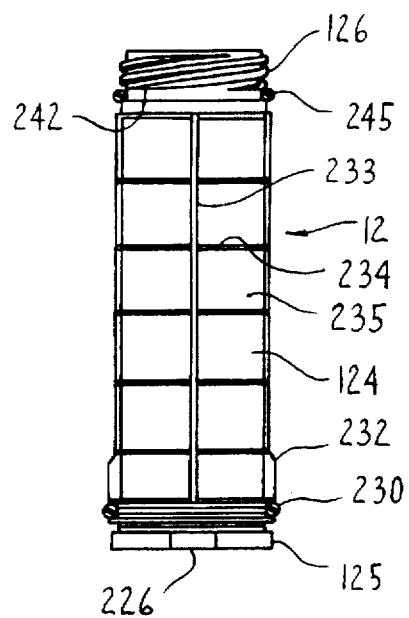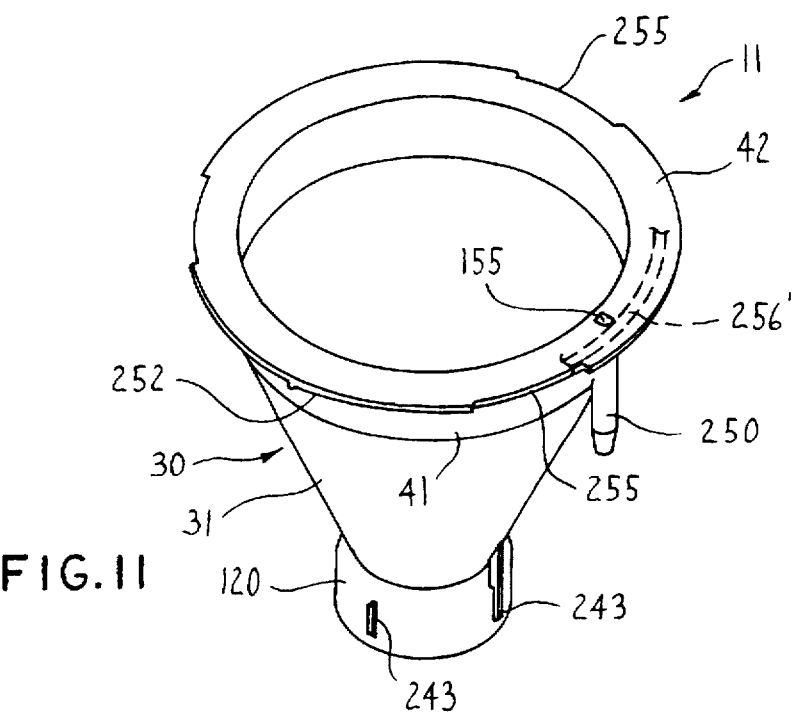

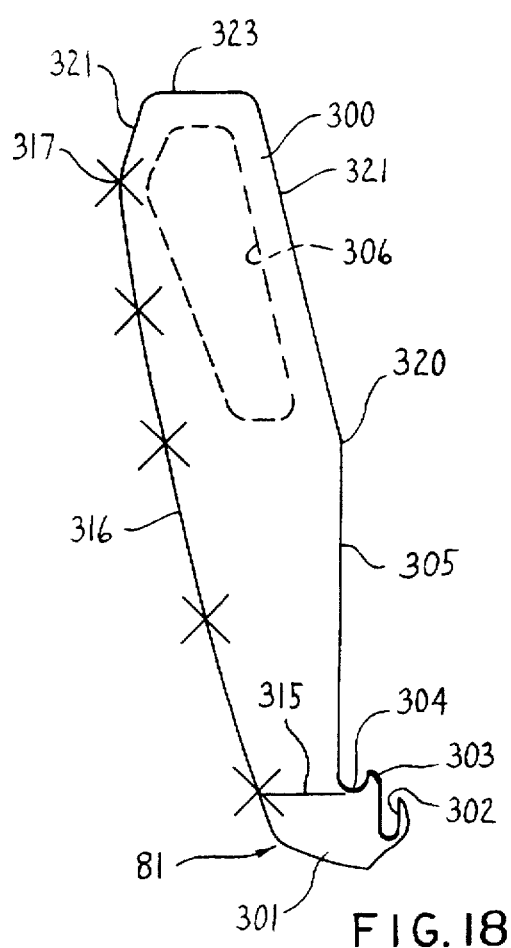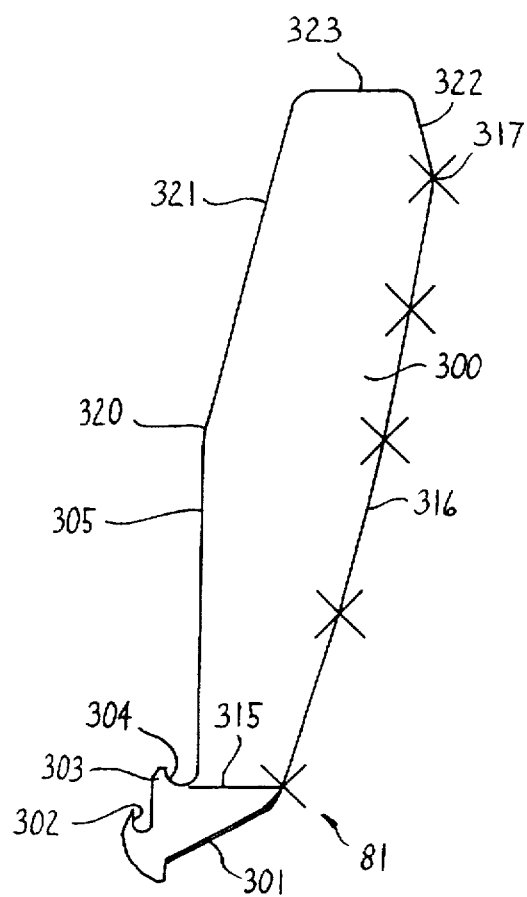

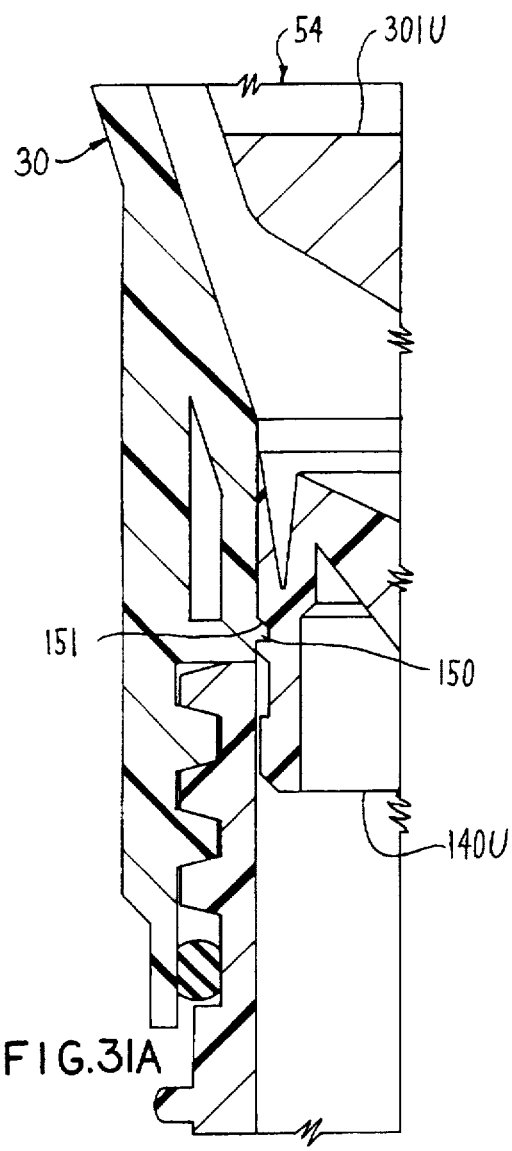 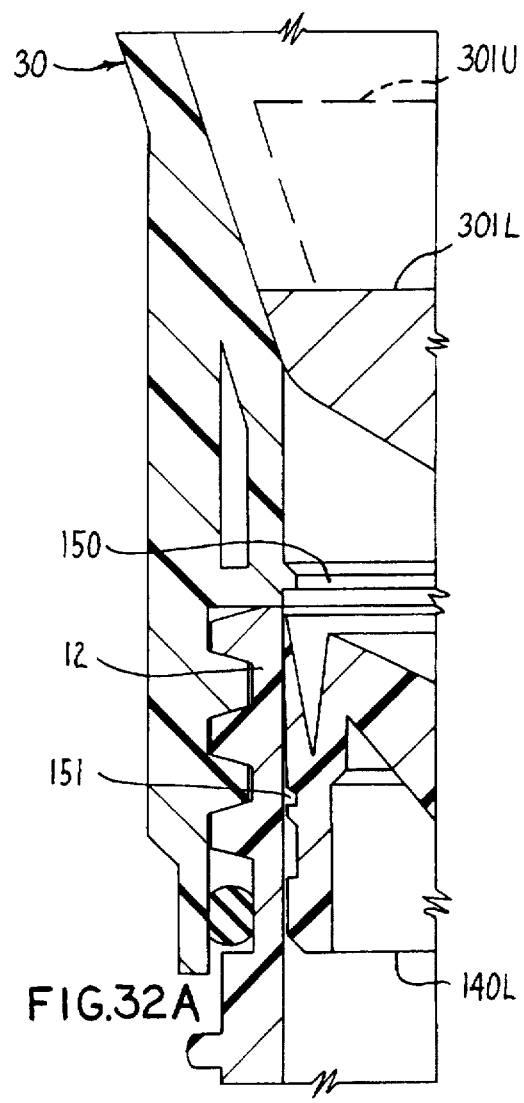
FIG.31A  FIG.32A
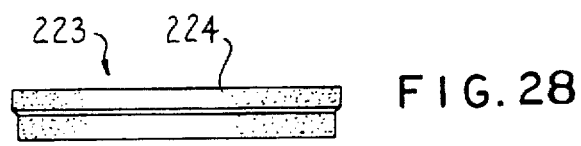
FIG.28
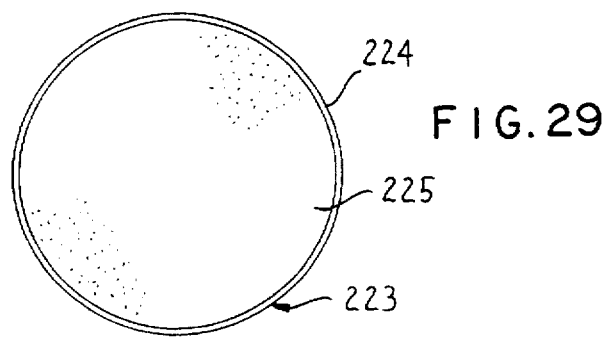
FIG.29

5,797,679

SURGICAL CEMENT MIXER APPARATUS

This application is a continuation of copending U.S. Ser. No. 08/599 253 filed Feb. 9, 1996 (attorney ref: Stryker IN Case 161).

FIELD OF THE INVENTION

This invention relates to an improved apparatus for mixing and loading a two-part cement of a type adapted for fixing a repair element to hard, rigid tissue in a patient (e.g. bone cement for fixing a prosthesis to bone, such as bone cement for fixing a hip stem in the femoral canal), and more particularly to such an apparatus for mixing and loading such cement under a partial vacuum (subatmospheric pressure).

BACKGROUND OF THE INVENTION

In orthopedic procedures it is common to use an acrylic bone cement to affix a prosthesis to the bone, for example a hip joint implant to the interior surfaces of the femur. Typically such bone cements are comprised of a liquid monomer and a solid polymer. The solid polymer contains the reaction initiator and is typically a finely divided powder. When the liquid monomer, which contains an activator, contacts the polymer, a reaction ensues that polymerizes the monomer around the polymer into a high molecular weight polymeric solid. It is known that when the monomer and polymer are mixed under a partial vacuum, the void volume (portion of the volume occupied by air or other gas bubbles) of the resultant high molecular weight polymeric solid is advantageously considerably less than when mixed in air at atmospheric pressure.

Resulting bone cements of this type have been applied to the surgical site in a variety of ways. One way is to use an extrusion device broadly similar to a caulking gun.

U.S. Pat. Nos. 5,265,956 and 5,344,232, and 5,415,474 assigned to the assignee of the present invention, disclose apparatus for mixing and loading a two-part bone cement mixer of the type suitable for fixing a prosthesis to bone in a surgical patient wherein the mixing and loading of cement is under a partial vacuum. This prior apparatus has proved quite satisfactory and, particularly in its ability to substantially exclude air bubbles from the cement during mixing and loading of the mixed cement into a cartridge for use thereafter in fixing a prosthesis to bone in a surgical patient (for example securing a hip stem prosthesis in the femoral canal of a patient).

The present invention arises from a continuing effort to improve on the apparatus disclosed in the aforementioned patents and the objects and purposes of the present invention include effecting such improvements.

An aspect of the present invention involves an improved apparatus for mixing a two-part cement of a type adapted for fixing a repair element to hard, rigid tissue of a patient and containing the mixed cement preparatory to dispensing for such fixation. Another aspect of the invention involves an apparatus comprising a mixing chamber having an outlet for mixed cement, a cartridge having an inlet releasably coupled to the outlet of the mixing chamber for receiving mixed cement therefrom, and means for moving the cement from an upper region of the mixing chamber down into a lower region thereof and then moving the mixed cement off the inner surface of the mixing chamber and into the cartridge.

Other objects and purposes of the invention will be apparent to persons acquainted with apparatus of this general type upon reading the following description and inspecting the accompanying drawings.

BRIEF DESCRIPTION OF THE DRAWINGS

FIG. 1B is a fragmentary cross-sectional view of the FIG. 1A apparatus with the cartridge removed and the funnel in a rest position in the base, following mixing and loading of cement.

FIG. 2A is an enlarged fragment of FIG. 2.

FIG. 9 is a central cross-sectional view of the cartridge of FIG. 1.

FIG. 10 is an elevational view of the FIG. 9 cartridge.

FIG. 11 is a pictorial view of the FIG. 1 funnel.

FIG. 18 is an elevational view of one blade of the blade unit taken on the plane of the blade.

FIG. 19 is a similar view of the other blade of the blade unit.

FIG. 28 is a side elevational view of the charcoal filter puck of FIG. 1C.

FIG. 29 is a bottom view thereof.

3

Figure 30:
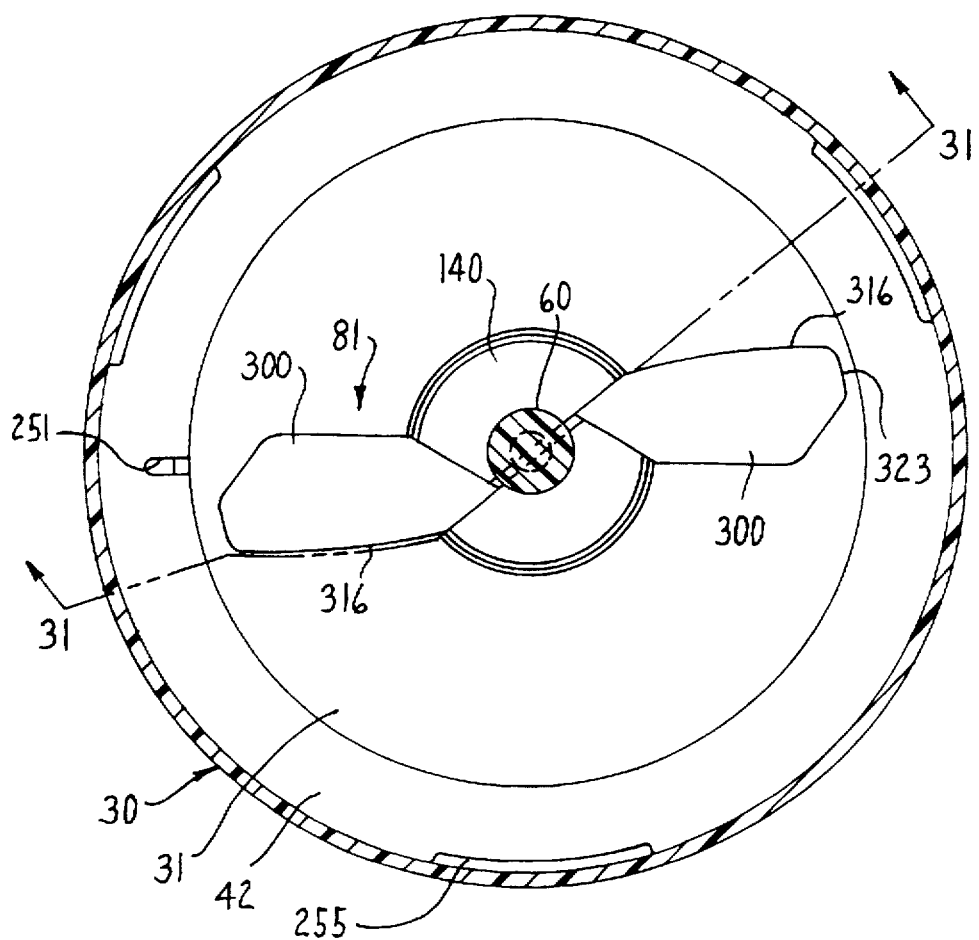
FIG. 30 is a sectional view substantially taken on the line 30—30 of FIG. 2, namely on the top plane of the funnel.
Figure 31:
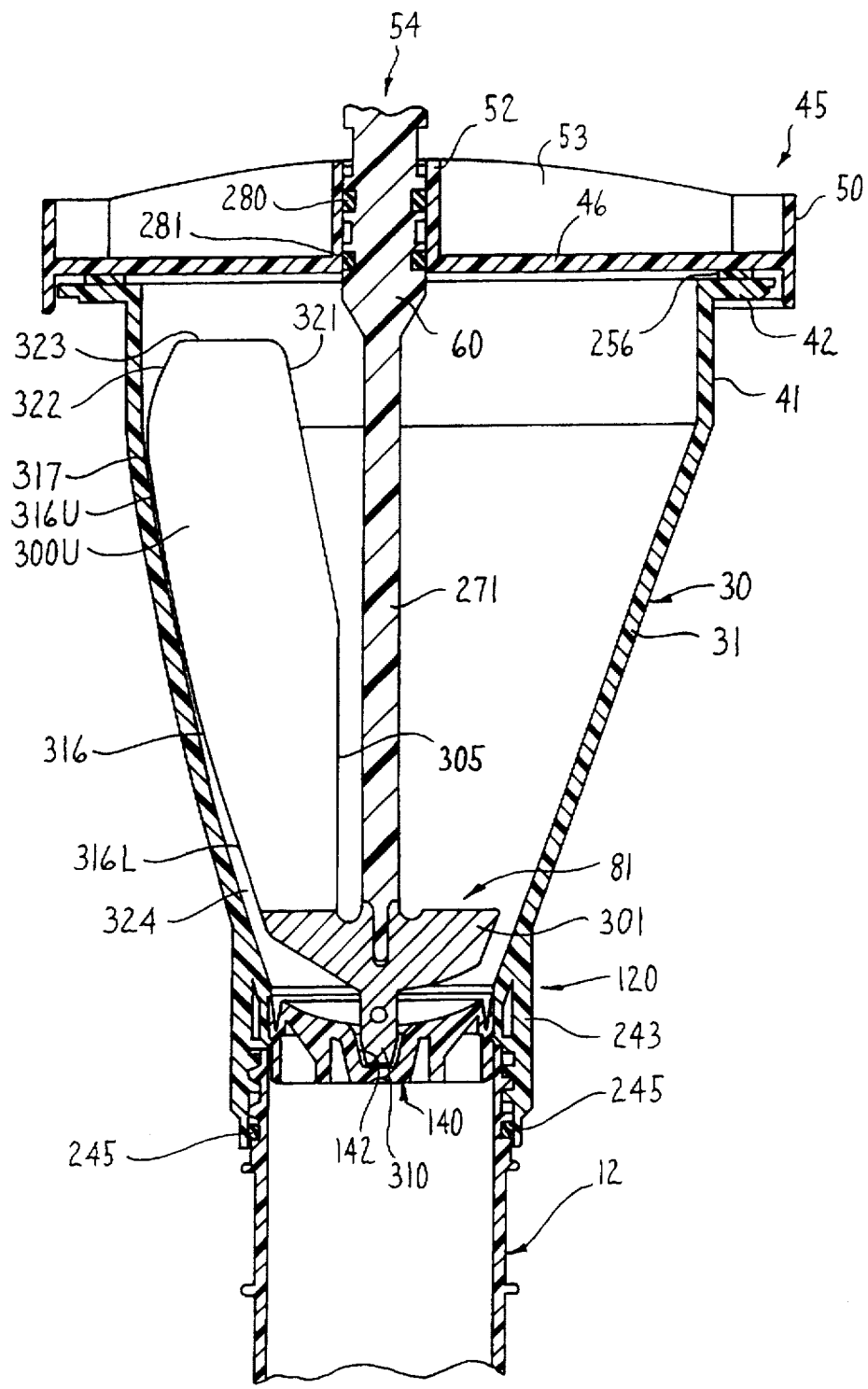

FIG. 31 is a sectional view substantially taken on the line 31—31 of FIG. 30, with the shaft assembly with upper, mixing position.

FIG. 31A is an enlarged fragment of FIG. 31.

Figure 32:
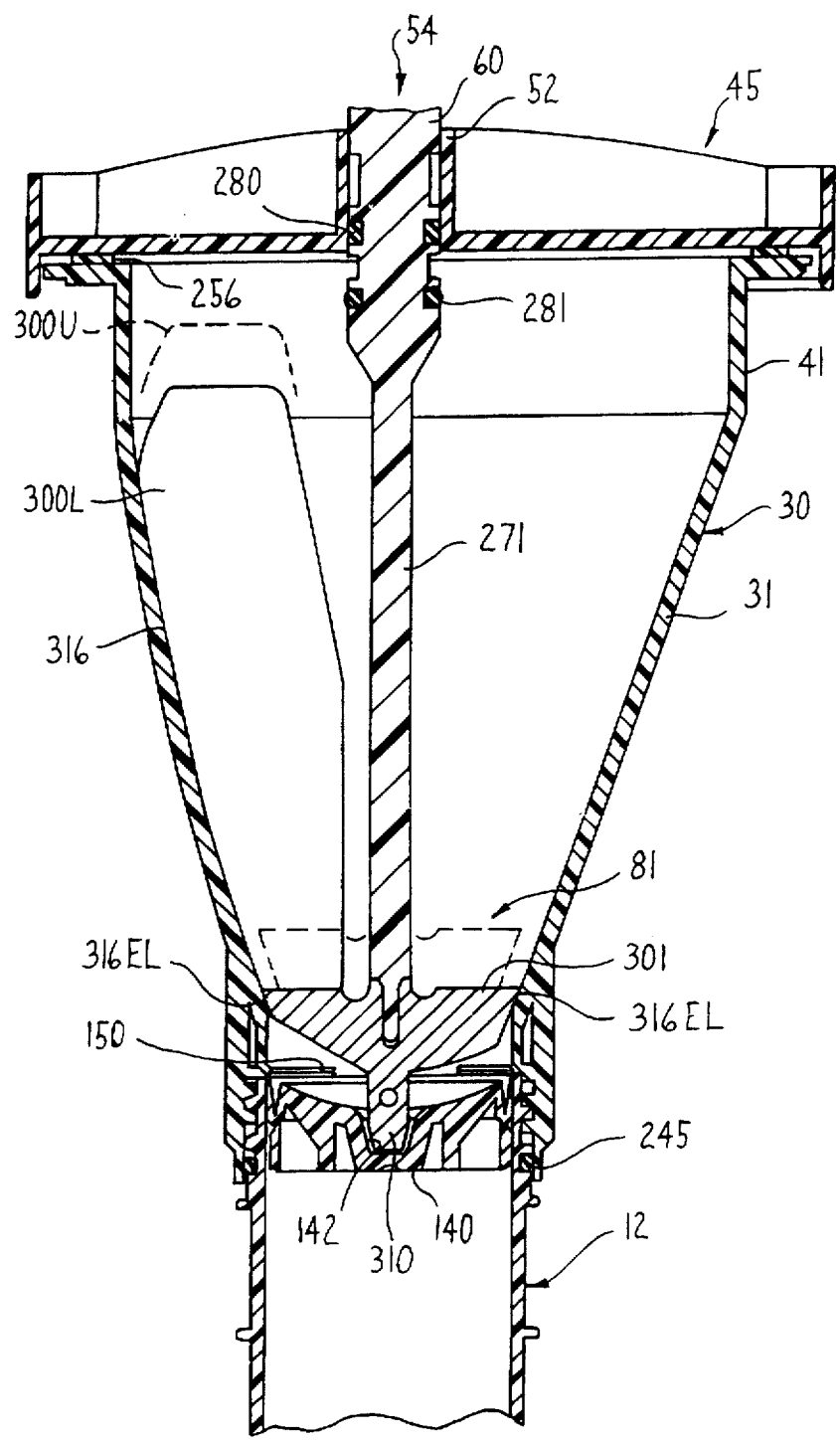

FIG. 32 is a view similar to FIG. 30 with the shaft assembly in its lower, loading position.

FIG. 32A is an enlarged fragment of FIG. 32.

DETAILED DESCRIPTION

A cement mixing and loading apparatus 10 (FIGS. 1A and 2), embodying the invention and particularly adapted for mixing two-part bone cement, comprises a mixing chamber 11 and a cartridge 12 located below the mixing chamber 11 for receiving mixed bone cement therefrom. A vacuum base 13 (FIG. 3) supports the mixing chamber and cartridge as hereafter discussed.

The mixing chamber 11 comprises an open-topped, downwardly converging funnel 30 (FIG. 2) whose sidewall is of frustoconical shape intermediate its upper and lower ends and through the major portion of its height. The frustoconical sidewall 31 of the funnel 30 is angled divergently upwardly at about 15° to 25° (here about 20°) to the vertical. The top of the funnel 30 has a relatively short cylindrical top portion 41 extending up from the conical sidewall 31 and surrounded by a horizontal radially outward extending annular flange 42. The flange 42 is preferably coaxial with the funnel 30.

A lid assembly 44 includes a lid 45 including a horizontal wall 46 (FIG. 2) bounded by a cylindrical perimeter flange 50 having portions extending both above and below the horizontal wall 46. The horizontal wall has an underlying seal ring (as at 256 hereafter discussed) to set on and seal against the flange 42 of funnel 30. The bottom portion of the cylindrical perimeter flange 50 snugly but vertically slidably surrounds the funnel top flange 42 to prevent sideways displacement of the lid assembly 44 with respect to the funnel 30.

A cylindrical hub 52 is fixedly upstanding from the top of the horizontal wall 46 of the lid in coaxial relation therewith. Plate-like spokes 53 radiate from the hub 52 out of the perimeter flange 50 to increase the rigidity of the horizontal wall 46 of the lid 45.

The hub 52 rotatably supports a shaft assembly 54 (FIG. 2) pendent coaxially therefrom. The shaft assembly 54 depends into the funnel 30 when the lid assembly 44 closes the top of the funnel 30.

The shaft assembly 54 (FIG. 2) comprises a head 60. The head 60 is rotatably and sealingly supported within the lid hub 52. A vacuum tight seal between the shaft assembly 54 and lid 45 prevents passage of air therepast into the mixing chamber 11.

A manually rotatable crank handle 70 (FIG. 2) is fixed at the top of the shaft head 60. The end of the crank handle remote from the shaft head 60 rotatably supports an upstanding, hand engageable knob 78 orbitable to rotate the shaft assembly 54. Rotation of the handle 70 positively rotates the shaft assembly 54.

Figure 1:
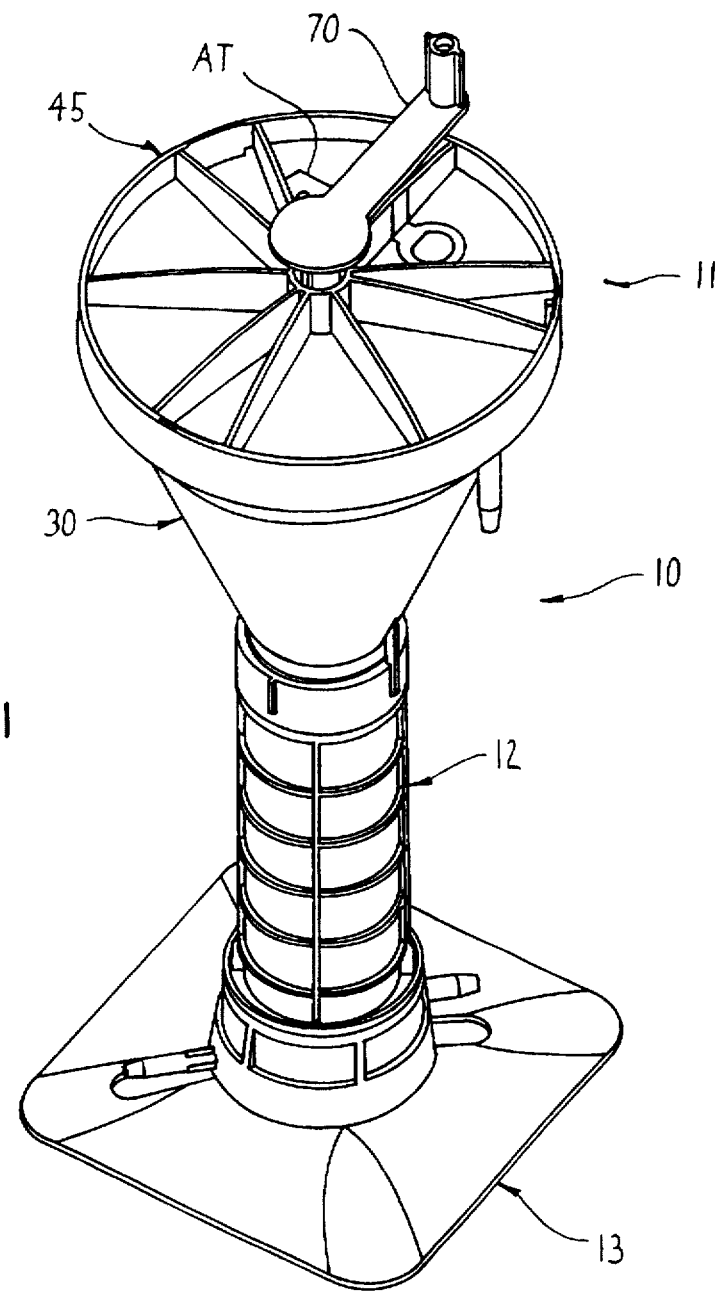
FIG. 1 is a pictorial view of an apparatus embodying the invention.
Figures 1A, 2:
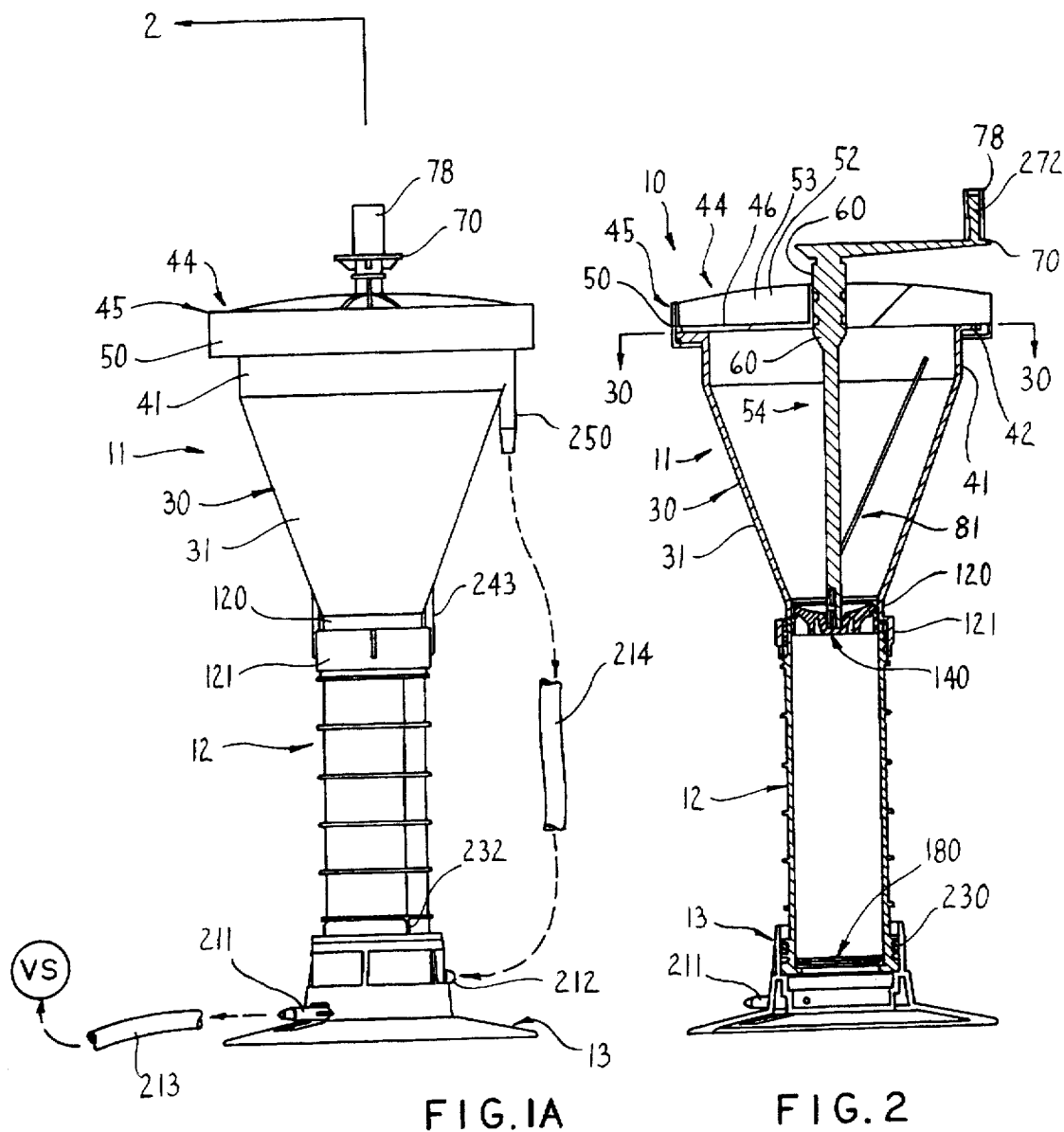
FIG. 1A is a front elevational view of the FIG. 1 apparatus.
FIG. 2 is a central cross-sectional view of the FIG. 1A apparatus.

The bottom of the shaft assembly 54 includes a blade unit 81 (FIG. 2).

Figure 13A:
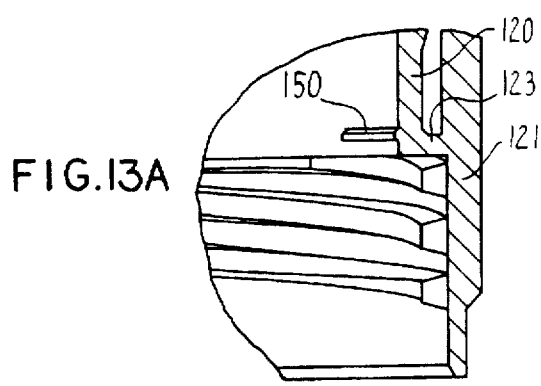
FIG. 13A is an enlarged fragment of FIG. 13.
Figure 13:
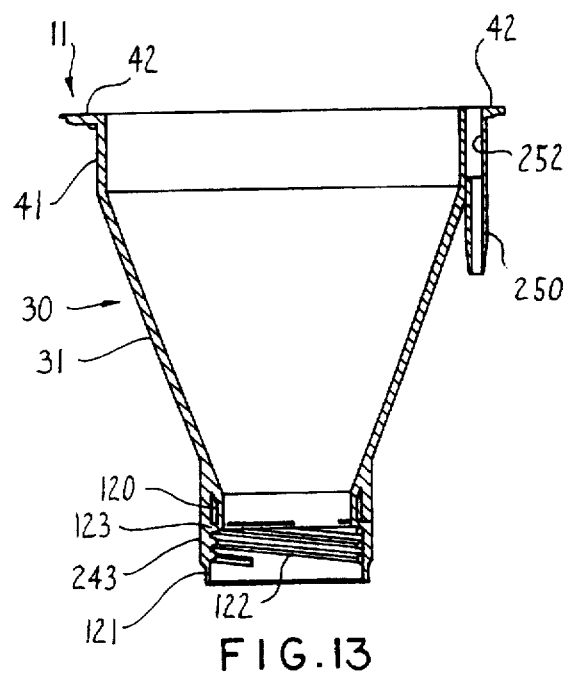
FIG. 13 is a central cross-sectional view of the FIG. 12 funnel.

The funnel 30 (FIG. 2) has a cylindrical outlet portion 120 integrally and coaxially dependent from the bottom of the conical portion 31. A connector sleeve 121 integrally and coaxially depends from the cylindrical outlet portion 120, is radially enlarged from the cylindrical outlet portion 120, and has internal threads 122 (FIG. 13). The threaded connector sleeve 121 at its top integrally connects to the coaxial, smaller diameter cylindrical outlet portion 120 by a radially inward extending flange 123.

As seen in FIGS. 2 and 9, the cartridge 12 comprises a hollow tube 124, open at its upper and lower ends, and provided at its lower end with a radially outwardly extending flange 125 for removable connection to a gunlike cement ejector (not shown). Various types of cement ejector (dispenser) guns are known and a preferred one is disclosed in corresponding U.S. Pat. No. 5,431,654, assigned to the assignee of the present invention. The flange 125 can thus be called a gun mount flange. The cartridge 12 also has a radially inwardly extending flange 127 (FIG. 9) at the bottom of the tube 124.

The upper end of the cartridge tube 124 is externally threaded at 126. The external threads 126 serve two purposes.

First, during loading of the cartridge 12 with mixed cement, as hereafter discussed, the threaded upper end 126 of the cartridge tube 124 is fixedly but releasably coaxially threaded up into the internal threads 122 of the threaded connection sleeve 121 and against the flange 123, to fix the cartridge 12 to the bottom of the mixing chamber 11 for filling with cement mixture. The interior walls of the funnel cylindrical outlet portion 120 and cartridge tube 124 are of substantially the same diameter and axially abut, so as to axially smoothly continue one into the other without discontinuity, for smooth filling of the cartridge with mixed cement from the funnel.

The second purpose served by the threads 126 on the top of the cartridge 12 is to threadedly receive, after the cartridge 12 is filled with cement mixture and removed from the mixing apparatus 10, the internally threaded end 130 of a cement injection nozzle of any convenient type and represented in above-mentioned U.S. Pat. No. 5,431,654 by way of example at 13. It will be understood that a variety of injector nozzles can be fitted to the threaded end 126 of the cartridge 12.

Figure 6:
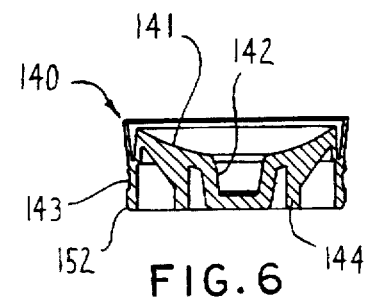
FIG. 6 is a central cross sectional view of the primary piston of FIG. 1C.
Figure 7:
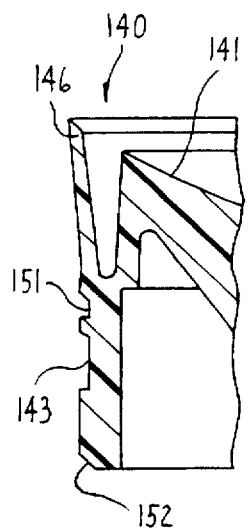
FIG. 7 is an enlarged fragment of FIG. 6.
Figure 8:
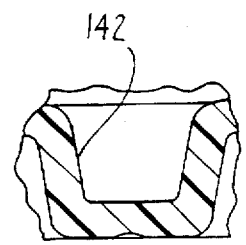
FIG. 8 is an enlarged fragment of FIG. 6.

A piston 140 (FIGS. 2, 6 and 7) here comprises a circular, generally puck-shaped member comprising an upwardly concavely curved top 141 (FIG. 6) having a relatively narrow central depression 142. The piston 140 further includes a substantially cylindrical peripheral wall 143 depending from the periphery of the top 141 and an annular cylindrical reinforcing flange 144 depending from the top 141 in radially spaced relation between the depression 142 and peripheral wall 143. The upper portion (for example the upper ¼ to ⅓) of the piston peripheral wall 143 is separated from the central portion of the piston 140 by a narrow, upfacing annular groove 145 and thereby forms an upstanding and somewhat radially outwardly biased annular feather seal 146. The annular feather seal 146 pushes radially outward against, and thus seals against, the surrounding internal cylindrical surface of the lower end portion of the funnel 30 in the upper position of the piston shown in FIG. 2. It will be understood that the upstanding annular feather seal 146 similarly bears resiliently and sealingly against the interior surface of the cartridge tube 124 after the piston has been pushed down into the cartridge 12, as hereafter described.

The downward and radially outward pressure of fluid cement components and mixed cement, against the top of the piston 140, presses the feather seal 146 even more firmly radially out against the surrounding interior walls of the funnel bottom portion and (later) the cartridge tube, to further improve the effectiveness of the feather seal 146.

Nevertheless, the orientation of the feather seal 146 allows it to slide easily downward, in a wiping manner, along such surrounding walls, without any tendency to catch or snag, so as not to interfere with easy downward sliding of the piston 140.

The piston 140 is initially positioned in the cylindrical outlet 120 of the mixing chamber 11. The piston 140 is resiliently held in this position by a resilient detent here comprising an interrupted circumferential bead 150 (FIG. 13A) radially inward extending from the interior face of the outlet 120, which bead 150 snaps into a correspondingly shaped outwardly opening annular groove 151 (FIG. 9) in the cylindrical sidewall 143 of the piston 140. In this position, the piston 140, with its peripheral feather seal 146, plugs the bottom of the mixing chamber 11 prior to and during mixing so that the cement components cannot escape from the funnel 30 downward into the cartridge 12. On the other hand, after mixing is completed, a modest downward pressure, manually exerted by the user, overcomes the resilient detent at 150, 151 and displaces the piston 140 downward past the bead 150, out of engagement with the funnel 30 and into the top of the cartridge tube 124. The bead 150 and groove 151 have radially inward and downward sloped top surfaces which cooperatively block accidental dropping of the piston 140 during mixing but allow intended downward displacement of the piston by the user. This geometry thus facilitates the transition of the piston from its seat in the funnel down into the cartridge. On the other hand, the bead 150 and groove 151 have bottom portions with a square edge which prevents the piston from moving upward. Therefore, force required to move the piston vertically upward is much greater than the force to move the piston vertically downward.

The bottom outer edge of the piston 140 is preferably chamfered at 152 (FIG. 7) to facilitate downward motion of the piston into the outlet portion of the mixing chamber 11 and thereafter into the cartridge 12.

The horizontal wall 46 of the lid 45 at a location spaced laterally from the hub 52, spokes 53 and perimeter flange 50 is provided with a small through hole 155 (FIG. 14) which is normally covered and sealed by a vacuum release label (e.g. adhesive tape) AT (FIG. 1).

In general, the components of the above-described apparatus 10 are of suitable rigid plastics materials. The piston 140 is preferably of molded high density polyethylene with a thin enough cross section in its annular feather seal 146 as to allow resilient inward bending thereof by the surrounding lower cylindrical portion 120 of the funnel as to create a seal therebetween. The blade unit 81 is preferably of stainless steel.

To the extent above described the apparatus is similar to that disclosed in U.S. Pat. Nos. 5,265,956 and 5,344,232 assigned to the assignee of the present invention.

Figure 25:
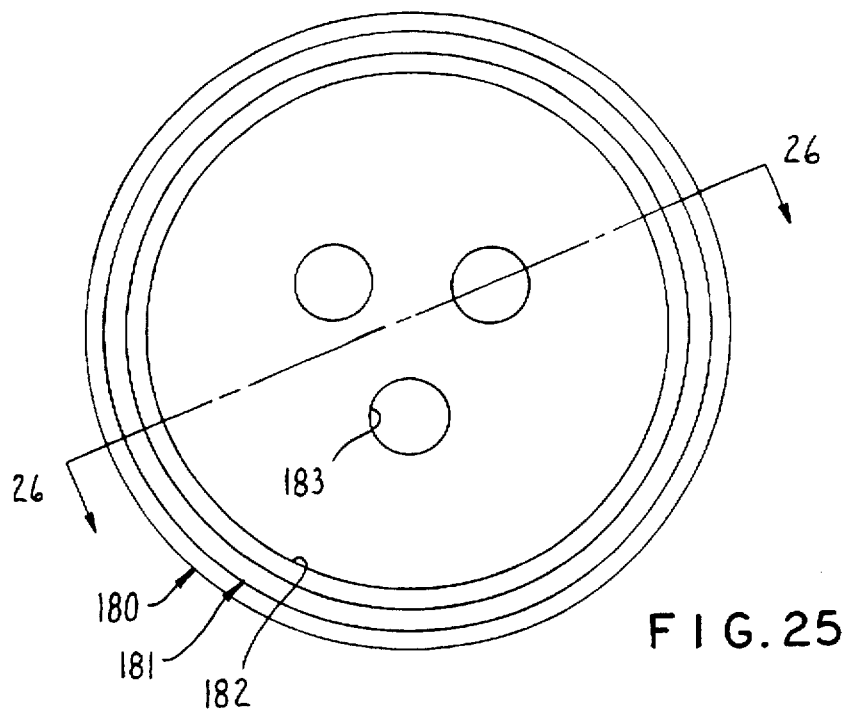
FIG. 25 is a plan view of the secondary piston of FIG. 1C.
Figure 26:
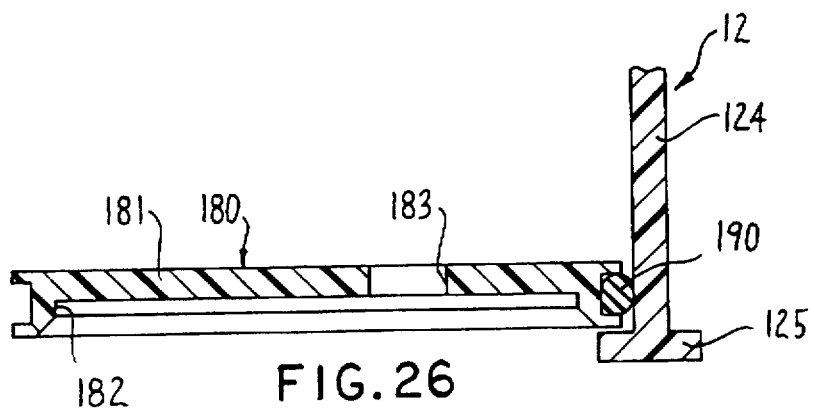
FIG. 26 is a fragmentary sectional view substantially taken on the line 26—26 of FIG. 25.
Figure 27:
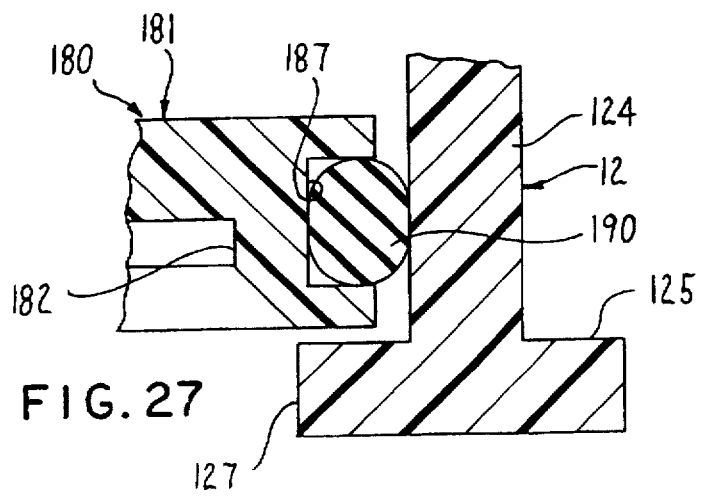
FIG. 27 is an expanded fragment of FIG. 26.

A secondary piston 180 (FIGS. 2 and 25–27) comprises a disk 181, whose bottom recessed at 182 and has central through holes 183 (FIGS. 25–27). The disk 181 is surrounded by an annular groove 187 receiving an O-ring 190. The O-ring 190 bears forceably and sealingly against the peripheral wall 124 of the cartridge 12 and preferably is radially crushed between wall 124 and annular groove 187 to provide a highly effective seal therebetween, so as to positively preclude bleeding of bone cement rearward past the secondary piston 180, e.g. even under the highest expected pressures exerted by the ram of a cement gun during all stages of filling of a femoral cavity with bone cement.

Whereas the upper primary piston 140 seals lightly enough against the interior wall of the cartridge 12 as to freely drop under the weight of mixed cement within the cartridge 12, after being dislodged from the outlet portion 120 of the funnel 30, the secondary (lower) piston 180 more firmly engages the interior wall of the cartridge 12 for more positive, high pressure sealing against loss of bone cement downwardly therepast, but requires more force to move it axially within the cartridge. Such force is easily supplied by the ram of a bone cement dispensing gun.

Unlike the primary piston 140, the secondary piston 180 stays at the bottom of the cartridge 12 during cement mixing and loading. After loading of the cartridge the primary piston 140 normally rests on the secondary piston 180. The secondary piston 180 blocks any bleed back of cement, around the primary piston 140, during dispensing by the gun. A very satisfactory dispensing gun is disclosed in aforementioned U.S. Pat. No. 5,431,654, assigned to the assignee of the present invention.

The secondary piston 180 preferably is of the type disclosed in U.S. Pat. No. 5,558,136 and assigned to the assignee of the present invention.

To the extent above described, the apparatus corresponds to that described in the aforementioned U.S. patents and application, assigned to the assignee of the present invention. While it is convenient to disclose the present invention in connection with such apparatus, it will be understood that the present invention is adaptable to use with other mixing/loading and injecting apparatus as well.

Attention is now directed to structure more directly bearing on the present invention.

In the preferred embodiment shown, the base 13 comprises a one-piece molded rigid plastic member including a rectangular foot 200 of shallow, generally frustoconical shape sloping up toward the center thereof and arranged to sit upon a supporting table or the like. The base foot 200 is slightly downwardly convex. The shallow frustoconical shape of the foot 200, which raises the central portion thereof above a supporting table, acts as something of a shock absorber to prevent direct impact of the central cup 201 and the apparatus thereabove against the table top, should the user drop or tap the apparatus downward onto the table surface, as to jar cement powder off the blades.

Figure 4:
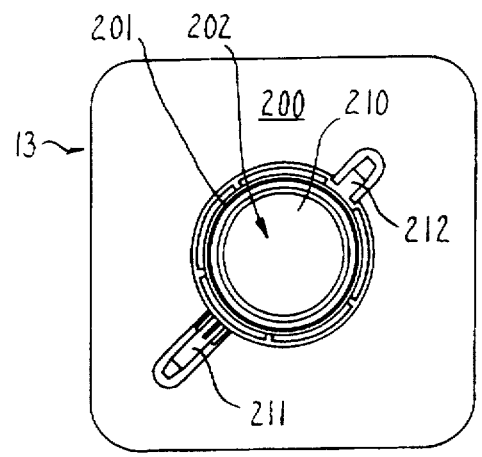
FIG. 4 is a top view of the FIG. 1 base.
Figure 5:
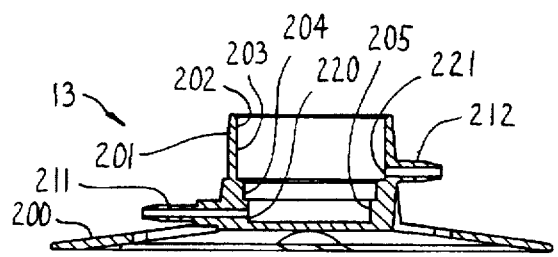
FIG. 5 is a cross-sectional view taken on the line 5—5 of FIG. 4.

A central cup 201 (FIGS. 3, 4 and 5) is coaxially upstanding from the central portion of the rectangular foot 200. The cup 201 is upward opening, of circular cross-section, and generally cylindrical defines an upward opening, circular cross-section cavity 202. The cavity 202 comprises, in succession, top, mid and bottom recesses 203, 204 and 205 (FIG. 5) which are circular, substantially cylindrical, of sequentially decreasing diameter and separated by upward facing annular steps 206 and 207. The bottom 210 of the bottom recess is closed and faces upward.

The vacuum base 13 further includes tubular vacuum nipples 211 and 212 protruding radially from preferably opposite sides of the central cup 201 in respective communication through ports 211 and 212 with the bottom recess 205 and top recess 203, near the bottom of the latter. The apparatus includes a length of plastic tubing 213 (FIG. 1A) sleeved over the lower nipple 211 and connectable to a conventional vacuum source VS for applying a partial vacuum to the bottom recess 205 of the base 13. The apparatus further similarly includes a further piece of plastic tubing 214 connecting the nipple 212 of the base 13 to a further, depending nipple, hereafter described, on and communicating with the interior of the funnel (funnel shaped mixing chamber) 30. In this way a suitable subatmospheric pressure can be applied to the top and bottom of the upper piston 140 (FIG. 2) to eliminate any pressure drop across the piston 140 as may tend to shift it up or down in an unwanted manner. More particularly, the subatmospheric pressure is applied to the interior of the funnel 30 and, through the central holes 183 (FIG. 25) in the lower piston 180, to the interior of the cartridge 12. The tubing 213 and 214 is flexibly bendable but of sufficient wall strength to not collapse and form a tube blockage under partial vacuum conditions. Such tubing 213 and 214 is widely available in a variety of sizes and quite inexpensive, is preferably of medical grade, and may for example be of the type commonly used in surgical irrigation tube sets. The tubing piece 214 is longer than the distance between the nipples to which it connects and preferably exceeds that distance by an amount sufficient to enable disconnection of the funnel 30, cartridge 12 and base 13. In the preferred embodiment shown, the tubing piece 214 is approximately 1 ½ to 2 times the height of the apparatus. This readily allows pulling the cartridge 12 upward out of the base 13, whereafter the cartridge can be unscrewed from the funnel 30, assembly being by a reversal of these steps.

Figure 3:
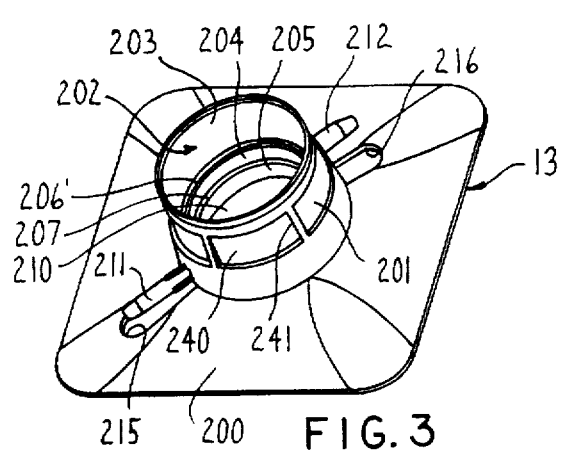
FIG. 3 is a pictorial view of the FIG. 1 base.

Elongate holes 215 and 216 in the foot 200 of the base 13, below the nipples 211 and 212 respectively, provide extra space to facilitate connection of the tubing pieces 213 and 214 respectively thereto (see for example FIG. 3). The elongate holes 215 and 216 in the base foot 200 also facilitate molding of the nipples 211 and 212 as an integral portion of the base 13.

Figure 23:
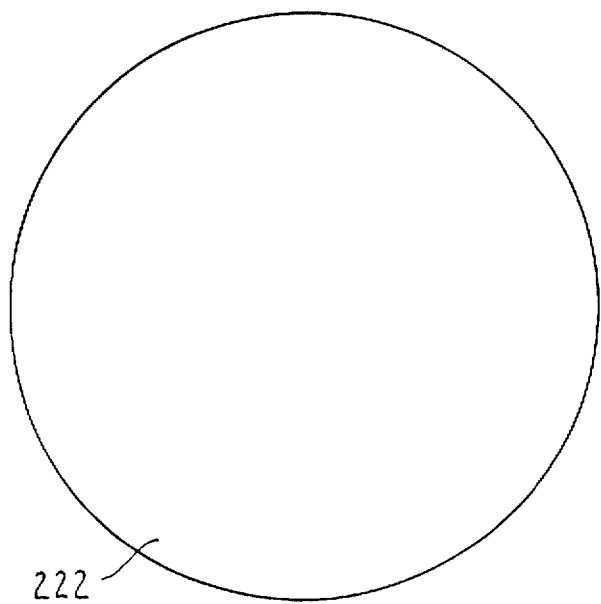
FIG. 23 is plan view of the filter disk of FIG. 1C.
Figure 24:
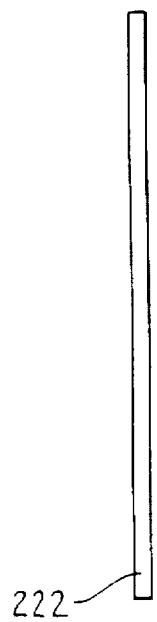
FIG. 24 is an edge view thereof.

The apparatus 10 includes means to prevent release of cement and cement components and fumes (vapors) from the funnel 30 and cartridge 12 to the vacuum nipple 211 leading to the vacuum source VS. In the preferred embodiment shown, such includes a microporous filter disk 222 (FIG. 2A, 23 and 24) which seats in the top recess 203 of the base 13 and rests atop the top step 206. The filter disk 222 is a snug press fit in the recess 203. The filter disk 222 tends to block downward flow of liquid, including bone cement liquids therethrough but allows airflow therethrough, and is located just below the port 221 of the nipple 212. The bottom of the cartridge 12 seats upon the filter disk 222. The radially outer flange 125 at the bottom of the cartridge 12 radially clears the inner wall of the top recess 203, providing an air space therebetween and allowing communication therethrough from the nipple 212 through the filter disk 222 into the mid-recess 204 of base 13.

In addition, the apparatus prevents passage of noxious bone cement fumes, passing downward through the filter disk 222, from entering the nipple 211 leading to the vacuum source VS, by provision of a microporous vapor filter puck 223 (FIG. 2A) preferably comprising a microporous sintered element of polyethylene and activated charcoal particles of small size arranged to allow passage of air axially therethrough but not of noxious fumes, which fumes are absorbed by the charcoal particles in the puck 223. The puck 223 has a top portion radially extended to form an annular flange 224 below the filter disk 222. The bottom portion 225 of the vapor filter puck 223 is slightly radially recessed to facilitate insertion in the mid-recess 204 and rests atop the lower step 207 above the bottom recess 205 of the base 13. The annular flange 224 of the vapor filter puck 223 is snugly fixed in the mid-recess 204 preferable by a radial press fit, as indicated in FIG. 2A.

In the preferred embodiment shown, the puck 223 is manufactured by sintering together polyethylene powder and ground activated charcoal to form a solid pierced by tortuous micro passages for airflow. The ground activated charcoal provides high surface contact area for high gas absorption rates despite the compact volume and thickness of the puck, particularly as compared to the prior art filter of above-mentioned patents. The disk 222 is a secondary filter here constructed of sintered polyethylene powder similar in porosity to the puck 223 but omitting the carbon particles. As a result, the disk 222 is white, rather than the black of the charcoal powder impregnated puck 223. The white disk is seated atop the black puck and, as seen from the top of the apparatus, makes the bottom of the funnel 30 look white and hence clean, which is desirable for aesthetic purposes and provides a barrier between the carbon filter and the surgical site.

The vacuum source VS is preferably a portable pump of any convenient type, normally located within the surgical operating room. Since the exhaust from the pump empties into the operating room it is desirable to at least partially remove the noxious vapors released by cement components before exhausting the vacuum pump into the surgical operating room, and it is the vapor filter puck 223 which accomplishes this.

In the preferred embodiment shown, the filter disk 222 is constructed of a material commercially available from Porex Technologies located at Fairbur, Ga., and the vapor filter puck 223 is constructed of a composition also available from Porex Technologies.

In addition to a radial clearance between the cartridge flange 125 and the inner surface of the top recess 203 of the base 13, the cartridge flange 125 may also, if desired, be provided with one or more flats, as indicated for example at 226 in FIG. 10. In addition, an annular groove 227 (FIG. 2A) immediately above the flange 125 provides additional circulation around the bottom portion of the cartridge and within the base top recess 203. The annular space around the bottom flange 125 of the cartridge 12 is isolated from the atmosphere by an O-ring 230 disposed in an annular groove 213 in the cartridge 12 just above the groove 227. Accordingly, a partial vacuum at the nipple 211 is prevented from drawing atmospheric air from between the top of the base 13 and cartridge 12, but does draw air downward from the cartridge 12 and nipple 212, without risk of contamination by liquid bone cement through the cartridge 12 (should any leak past the two pistons therein during loading) and from the top of the funnel 30 as hereafter discussed.

The O-ring 230 also provides the cartridge 12 with a snug friction fit in the base 13, requiring a positive and intentional force by the user to separate the two and so that casual handling of the apparatus (e.g. picking up the apparatus by means of the cartridge 12 or funnel 13, or jarring or shaking the apparatus) will not accidently dislodge the base 13 from the bottom of the cartridge 12.

The top recess 203 of the base 13 is sized to snugly frictionally receive not only the bottom of the cartridge 12, but also, after separation of the cartridge 12 from the base 13 and funnel 30, the outlet portion 120 at the bottom of the funnel, as well.

Thus, after cement has been mixed and loaded from the funnel 30 into the cartridge 12, and the cartridge 12 has been removed for insertion in an injection gun, the bottom portion 121 of the funnel can be seated in the top recess 203 of the base 13 to provide a secure resting place for the funnel 30, so that it does not tip over and, more importantly, so that any residual bone cement unintentionally left in the funnel cannot flow onto surfaces of the surgical operating room, but rather can only drain into the top recess 203 of the base 13

(FIG. 1B). The base 13 thus acts at this time as a stopper or closure for the bottom of the funnel 30, in addition to securely supporting the funnel 30 in an upright position. Bone cement and vapor leakage from the bottom of the funnel is thus prevented by the filter disk 222 and puck 223. This is true whether or not the user remembers to disconnect the vacuum hose 213 from the vacuum source VS, so that neither left over bone cement nor significant vapors therefrom can reach the vacuum source VS or leak into the surgical operating room from the bottom of the funnel 30. By leaving the lid assembly 44 in place, as shown in FIG. 1 and 2, leakage of bone cement or bone cement vapors from the top of the funnel can be prevented as well. In this way, significant bone cement vapors are not permitted to leak into the surgical operating room during or following bone cement mixing and loading.

The base 13 and tubing piece 214 replace the vacuum shroud and the filter (connected in the vacuum line between the vacuum shroud and the vacuum source) in the prior apparatus of above-mentioned U.S. Pat. No. 5,265,956. In such prior apparatus, the vacuum shroud was necessarily made of a rigid metal material and was sufficiently costly as to not economically be a single use disposable item, but rather had to be recovered for reuse, which involved time and effort and hence cost to clean same and inventory and sterilize same for reuse. Accordingly such vacuum shroud involved substantial cost both initially and to reuse. The base 13 in the present invention saves the cost of the vacuum shroud (initial and refurbishing) in that the base 13 in the present invention, including the filter disk 222 and puck 223, is providable for substantially the cost of the vacuum line filter in the prior apparatus, which line filter it eliminates. Indeed, the present cost of the base 13 is very little more (e.g., 10¢) than the prior inline filter.

Elimination of the shroud of the prior apparatus avoids further prior problems. More particularly, occasionally the user, upon removing the loaded cartridge, would simply set the mixing funnel atop the shroud. This allowed residual mixed cement in the funnel to drip downwardly into the shroud, which cement would then harden and have to be hand cleaned from the shroud before the shroud could be reused. Moreover, because of the height of the shroud, casually setting the used funnel atop the prior shroud risked accidental knocking over of the combination and hence spilling of any residual cement in the funnel, if carelessly left in the way of working surgical personnel. These problems are eliminated by the present invention by elimination of the prior shroud.

Upstanding fins 232 (here 4 in number) are evenly circumferentially spaced on the bottom portion of the cartridge 12 just above the O-ring 230 and are an easy sliding fit into the top recess 203 of the base central cup 201. The fins 232 (FIGS. 9 and 10) extend up above the top of the cup 201, with the cartridge installed therein (as seen in FIGS. 1A and 2) to prevent tilting of the cartridge more than a couple of degrees from co-axiality with the base during handling of the apparatus, without requiring a close tolerance cylindrical surface to cylindrical surface siding fit of the cartridge 12 into the top of the base 13.

The cartridge 12 is preferably provided with spaced, axially and circumferentially extending ribs 233 and 234. Such ribs may serve as radial reinforcement for the elongate cylindrical mid-portion 235 (FIG. 10) of the cartridge 12 and, in addition, provide a high friction handgrip to facilitate removal of the filled cartridge from the funnel and base. To this end, the central cup exterior of the base 13 is preferably also provided with the textured handgrip, here in the form of indents 240 (FIG. 3) circumferentially spaced by axial ribs 241.

The cartridge 12, near its upper end and just below the top external threads 126 thereof, includes an annular groove 242 (FIGS. 9 and 10) for receiving an O-ring 245 for sealing engagement with the lower interior portion of the outlet sleeve 121 of the funnel 30, just below the threads 122 (FIG. 13) thereof. See also FIG. 2A. Thus, the upper end of the cartridge 12 threads snugly into the threaded connecting sleeve 121 of the funnel 30 and is sealed with respect thereto, against entry of air, by the O-ring 245. On the other hand, the bottom of the cartridge 12 pushes axially downward into the central cup 201 of the base 13 and is sealed against air leakage therebetween by the O-ring 230. Thus, the base and cartridge 12, when coupled together as shown in FIG. 2, can be evacuated at the vacuum nipple 211 to apply subatmospheric pressure below the upper piston 140 and through tube 214 to the upper portion of the funnel 30, to equalize the subatmospheric pressures above and below the piston during mixing.

Figure 12:
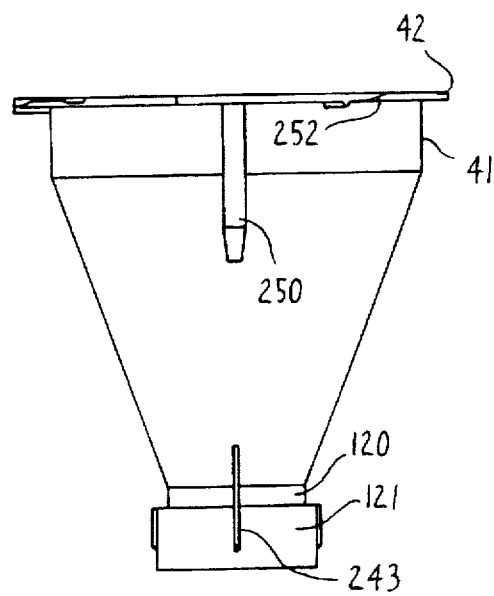
FIG. 12 is a side elevational view of the FIG. 1 funnel.

The bottom portion of the funnel 30, in the region of the outlet portion 120, is provided with circumferentially spaced axially extending external fins 243 (FIGS. 1B, 11 and 12), here four in number. In the particular embodiment shown, two diametrally opposed fins 243 extend upward to the frustoconical side wall 31 of the funnel 30 and the other two diametrally opposed fins 243 do not extend above the top of the sleeve 121. The fins 243 extend the majority of the length of the sleeve 121 but terminate below the bottom thereof in chamfered bottom edges 244. With the cartridge 12 removed from the apparatus after filling, the funnel 30 can be displaced downwardly to rest with its connector sleeve 121 in the upper recess 203 of the base 13, the bottom of the sleeve 121 resting upon the filter disk 222. The chamfered bottom ends 244 of the fins 243 help guide the bottom of the funnel 30 downward into the base 13. The fins 243 slide easily, with generous clearance, down into the recess 203 but once there, they prevent tipping through more than a few degrees of the funnel 30 with respect to the base 13, in much the same way as the fins 232, above discussed, on the bottom portion of the cartridge 12 prevent tipping of the cartridge 12 during filling.

The funnel 30 includes a depending nipple 250 (FIGS. 1A, 11 and 13) molded into and depending from the cylindrical top portion 41 of the funnel and containing an open ended vacuum passage 251 (FIG. 13) which opens out through the hole 155' in the radially inner portion of the radially outwardly extending top flange 42 of the funnel. The vacuum tubing 214 above discussed connects at its upper end to the nipple 250 to apply subatmospheric pressure therethrough to the underside of the lid 45 and hence to the interior of the funnel 30.

Figure 14:
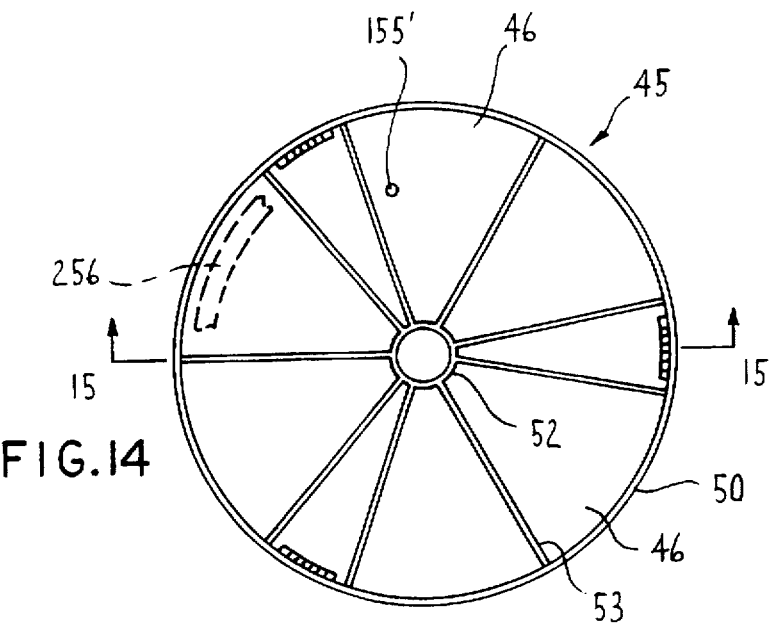
FIG. 14 is a top view of the transparent cover of FIG. 1.
Figure 15:
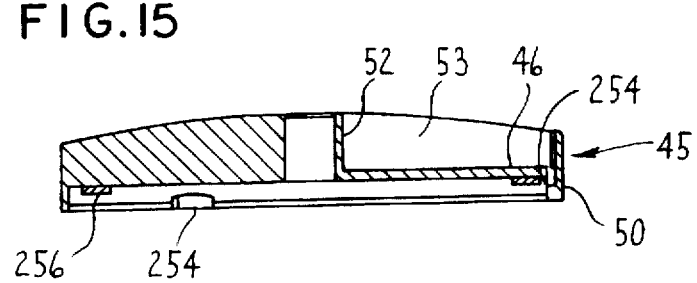
FIG. 15 is a sectional view substantially taken on the line 15—15 of FIG. 14.

In the preferred embodiment shown, the lid 45 is removably but fixedly securable atop the funnel 30 by a positive connecting means and does not rely on the pressure drop, from outside atmospheric pressure to subatmospheric pressure within the funnel, to hold the lid in place upon the funnel. More particularly, a partial turn threaded connection, generally bayonet like in character, fixedly but releasably secures the lid on the funnel to close the upper end of the latter. This connection comprises a plurality (here 3) of evenly circumferentially spaced circumferential ramps (or partial threads) 252 (FIGS. 11 and 12) formed in the underside of the funnel flange 42, provided with end stops 253 and coacting with tabs 254 (FIG. 14) radially inward extending from near the bottom of the lid perimeter flange 50 (FIGS. 14 and 15). The tabs 254 are insertable downward through radially outwardly and vertically opening notches 255 (FIG. 11) in the outer edge of the funnel flange 42, whereupon rotation of the lid upon the top of the funnel engages the tabs 254 with the lead-in portion of the corresponding circumferential ramps 252 on the underside of the funnel flange 42, such that rotation of the lid on the funnel through less than ⅕ turn draws the lid tightly down atop the funnel flange as the tabs 254 proceed circumferentially downward along the corresponding circumferential ramps 252.

A generally flat, circumferential seal ring 256 (in the preferred embodiment shown, a flat seal ring) is of soft, closed pore, plastic foam material, and is adhesively bonded to the bottom of the horizontal wall 46 of the lid 45. The seal ring 256 is located as shown, in a circumferentially fragmentary manner, in FIGS. 14 and 15. The location of the seal ring 256, with the lid atop the funnel, is indicated in dotted line, in a circumferentially fragmentary manner, at 256' in FIG. 11, from which it will be seen that the seal 256 is disposed radially between the vacuum passage 251 and notches 255, with the lid seated upon the funnel 30. Thus, with the lid seated atop the funnel 30 by interaction of the ramps 252 and tabs 254, the seal ring 256 provides a vacuum tight seal between the lid and funnel to close the top of the funnel vacuum tight. The lid can be threaded onto and off of the funnel as desired by the user.

The vacuum release hole 155 (FIG. 14) through the lid horizontal wall 46 is normally closed by its covering adhesive tape AT (FIG. 1) until mixing is completed and the cartridge is loaded with mixed cement. When it is desired to separate the loaded cartridge 12 from the funnel and base the adhesive tape AT is removed from the hole 155 to allow atmospheric pressure to enter the funnel. In the particular embodiment shown, the hose 214 connecting the vented funnel to the base 13 likewise applies atmospheric pressure from the funnel to the upper portion of the base cup 201 above the filter disk 222 (to similarly vent the base cup 201). This equalizes the pressure on the opposite ends of the cartridge 12 (placing same at atmospheric pressure) to ease removal of the cartridge from the funnel and base, without resistance due to a pressure drop from outside to inside the cartridge.

Figure 20:
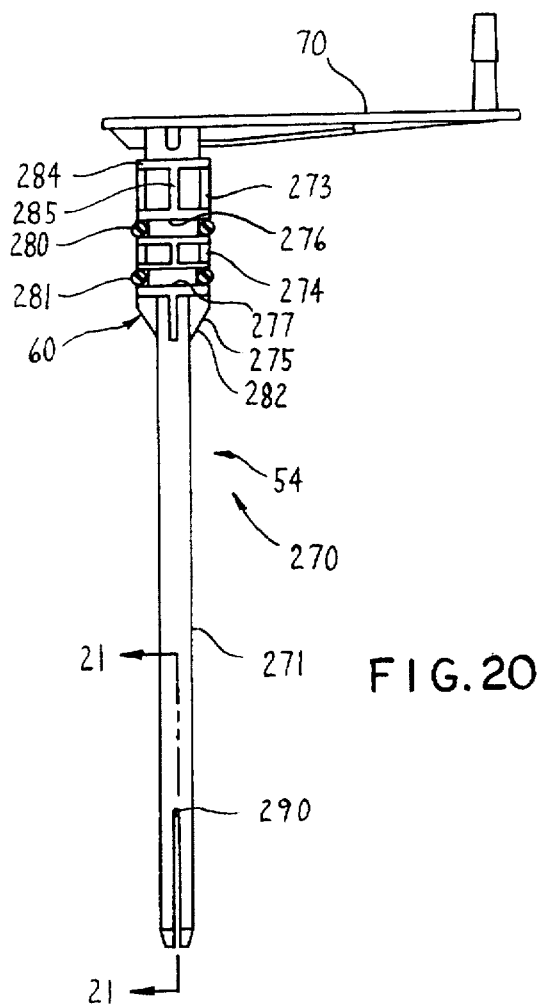
FIG. 20 is an elevational view of the shaft unit.
Figure 22:
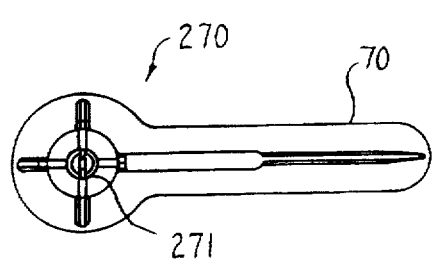
FIG. 22 is a bottom view of the shaft unit of FIG. 20.
Figures 21, 21A:
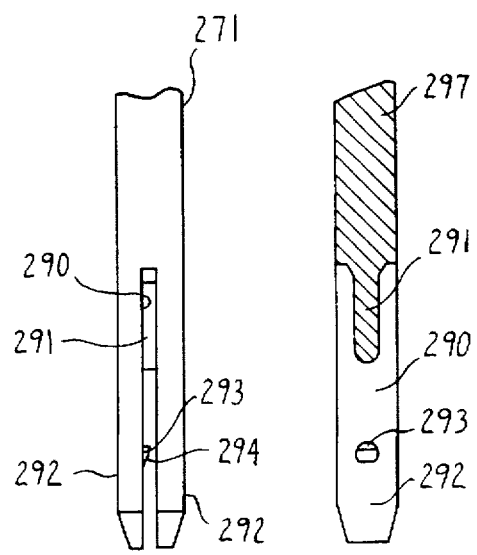
FIG. 21 is an enlarged fragmentary sectional view substantially taken on line 21—21 of FIG. 20.
FIG. 21A is an enlarged fragment of the bottom portion of the shaft of FIG. 20.

In the preferred embodiment shown, the shaft assembly 54 (FIGS. 2, 16–22 and 30–32) comprises a one-piece shaft unit 270 (FIGS. 20–22) preferably molded of a rigid plastics material and including integrally therein the head 60 and crank handle 70 above-mentioned, as well as an elongate depending shaft 271. The shaft assembly 54 further includes a blade unit 81 (FIGS. 16–19), here a one-piece element formed of a substantially rigid material (preferably stainless steel, e.g. about 0.050 inch thick). If desired, a sleeve-like knob 78 may be located rotatably on a knob stub 272 (FIG. 2) integrally upstanding from the free end of the crank handle 70. The spinning knob 78 being optional since the knob stub 202 itself can be gripped by the user to rotate the shaft assembly. The crank handle 70 extends radially and integrally from the top of the head 60 of the shaft unit 270 (FIGS. 2 and 20).

The head 60 (FIG. 20) comprises top, mid and bottom radially enlarged portions 273, 274 and 275 separated by top and bottom annular grooves 276 and 277, provided with O-rings indicated in cross-section at 280 and 281, respectively. The bottom end of the bottom enlarged portion 275 is tapered at 282 to facilitate insertion of the head 60 into the lid hub 52. To save plastic molding material, the enlarged portions 273, 274 and 275 rather than being solid, are formed with recesses 283 bounded by circumferentially spaced and axially extending flanges 284 and 285. The O-rings 280 and 281 are axially spaced such that at least one thereof will be snugly and sealingly contained in the hub 52 of the lid 45 at all times, despite vertical repositioning of the shaft assembly 54 during use, with respect to the lid 45 and funnel 30.

Integrally and coaxially depending from the head 60 is a elongate, reduced diameter, rod-like shaft 271. The bottom portion of the shaft 271 has a diametral slot 290 (FIGS. 20 and 21) formed therein. An integral web 291 extends partway down into the slot 290 and extends diametrally across the slot in a plane at right angles to the plane of the slot, to bifurcate the upper portion of the slot. The slot 290 divides the bottom of the shaft 271 into diametrally opposed legs 292. A generally circular cross-section tooth 293 (FIGS. 21 and 21A) protrudes from one leg 292 about half way into the slot 290 and about half way between the bottom of the web 291 and bottom of the corresponding leg 292. The lower surface of the tooth 293 defines a ramp 294 and the top of the tooth defines a stop surface extending perpendicular to the leg 292 and facing upward toward the top of the slot 290.

Figure 17:
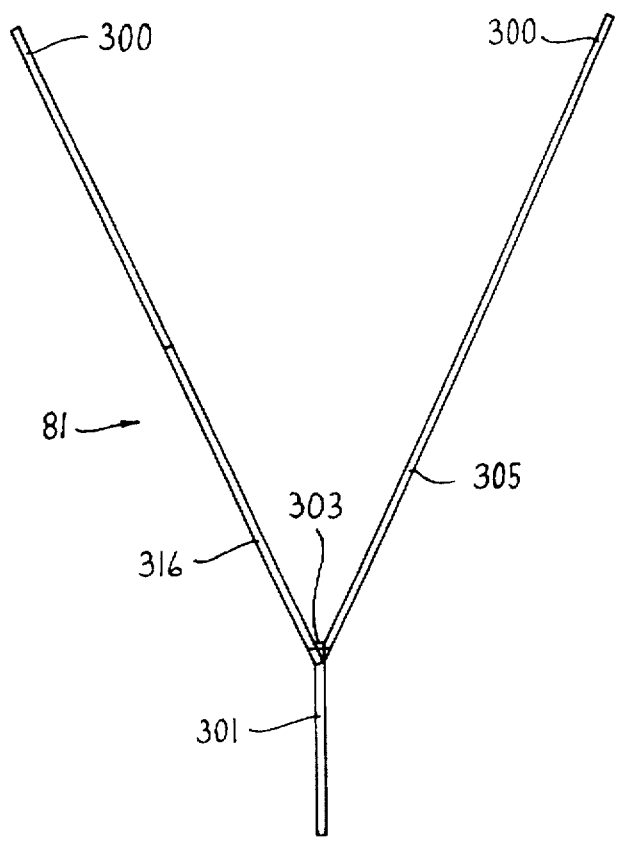
FIG. 17 is an edge-wise view of the blade unit of FIG. 1C.
Figure 16:
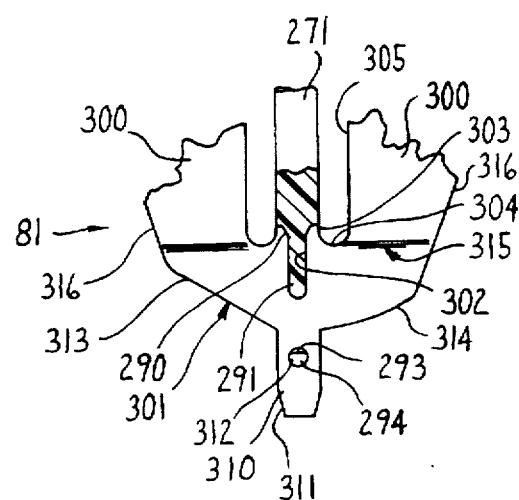
FIG. 16 is a fragmentary view of the assembled blade and shaft of FIG. 1C.

The blade unit 81 (FIGS. 17–19) is rigid metal sheet material, here stainless steel, of preferably about 0.040 to 0.055 inch thickness, preferably made by cutting, followed by bending of the blades 300 oppositely out of the plane of their common central support 301 (FIGS. 16 and 17). In the preferred embodiment shown, the wall 31 of the funnel 30 angles at about 20° to its vertical axis and the planes of the blades 300 each angle at about 23° to 27° from the plane of the support 301 (FIG. 17).

The support 301 (FIG. 16), on its central, rotational axis, has a deep upward opening central notch 302 flanked by upstanding ears 303 in turn flanked by shallow, upward opening, off-axis depressions 304. The remote edges of the depressions 304 continue upward to define preferably parallel, lower, inner side edges 305 of the blades 300. The blades 300 bend from the plane of the support 301 approximately along a line tangent to the bottoms of the depressions 304.

The support 301 includes a central depending tongue 310 with chamfered bottom corners 311. The tongue 310 has a central through hole 312 intermediate its top and bottom ends. At a point roughly half way between the bottom of the notch 302 and the hole 312, the support 301 widens from the top of the tongue 310 along upwardly and outwardly angled bottom support edges 313 and 314. In the embodiment shown, the bottom edges 313 and 314 are asymmetrical, in that the bottom edge 313 angles up along a straight line whereas the bottom edge 314 is slightly convexly rounded and laterally shorter than the edge 313. The bottom edges 313 and 314 terminate below the bend line 315. The blade outer edges 316 angle outward and upward from the outer ends of the support bottom edges 313 and 314.

To assemble the mixing chamber 11, O-rings 280 and 281 are placed on the enlarged shaft head 60 in their respective grooves.

The shaft 271 (FIG. 20) is then inserted down through the open hub 52 (FIG. 15) of the lid 45. The blade unit 81 (FIG. 17) is then rigidly fixed to the bottom of the shaft 271. This is done by inserting the central support 301 of the blade unit upwardly into the downward opening slot 290 of the shaft 271. As the central portion of the support 301 slides upward into the shaft slot 290, the blade notch 302 first receives the tooth 293 of the shaft and then slides up past it, slightly springing apart the shaft legs 292 in a resilient manner to do so. The blind end of the blade unit notch 302 is preferably rounded or chamfered to avoiding damaging the tooth 293 and to slide smoothly upward past it without catching on it.

As the blade unit 81 continues to move upward with respect to the shaft 271, the blade notch 302 receives the depending web 291 of the shaft. Upward movement of the blade unit 81 with respect to the shaft 271 positively stops when, as shown in FIG. 16, the tooth 293 of the shaft snaps laterally into the hole 312 in the blade tongue 310, the blade notch 302 substantially fully receives the shaft web 291, and the blade ears 303 substantially reach the top of the shaft slot 290. The downward facing tooth ramp 294, cammed by the blade support 301 resiliently springs apart the shaft legs 292 during upward insertion of the blade support 301 into the shaft slot 290. Once the blade support 301 is fully installed in the bottom portion of the shaft 271, as shown in FIG. 16, the shaft legs 292 spring resiliently back to firmly grip the shaft support 301 therebetween. Also, in the assembled condition of the blade unit 301 and shaft 271 shown in FIG. 16, the tooth 293 and depending web 291 of the shaft 271 firmly grip the opposed edge surfaces of the blade support 301 to prevent rocking of the blade unit in the plane of its support 301 and to prevent vertical movement of the blade unit with respect to the shaft 271. In this way, the blade unit 81 is fixedly connected to the bottom of the shaft 271 by a simple, single motion snap-fit insertion thereinto. It will be noted that the lid 45 is thus trapped on the shaft assembly 54 axially between the handle 70 and the blade unit 81 which, except for addition of the spinner knob 78, should one be desired, completes the assembly of the mixing chamber 11.

Thus it will be seen that the entire mixing chamber 11 is assembled quickly and easily with a minimum number of parts and steps, namely by sliding the O-rings 280 and 281 up the shaft 271 onto the head 60, inserting the shaft 271 down through below the hub 52, snapping the blade unit 81 into the bottom of the shaft 271, and rotating the lid 45 a partial turn onto the top of the funnel 30.

The blades 300 are, in the preferred embodiment shown, identical. The outer edge 316 of each blade angles upwardly and outwardly from the rotational axis of the shaft as seen in FIGS. 18 and 19, in a shallow convex curve to a point 317 near the top of the blade. The lower inner side edge 305 of each blade extends upward substantially parallel to the shaft axis to a point 320 spaced well below the point 317. The upper inner blade edge 321 and upper outer blade edge 322 converge gradually upward to the top edge 323 of the blade, which in the preferred embodiment shown is substantially flat and horizontal. The shape of the convex lower outer edge 316 of the blade 300 is determined by its working relationship with the frustoconical wall 31 of the mixing funnel 30.

The shaft assembly 54, including the blades 300, has a first (upper) operating position (the initial mixing position) shown in solid lines in FIG. 31 and dotted lines in FIG. 32, and a second (lower) operating position (the cartridge loading position) shown in solid lines in FIG. 32. These upper and lower operating positions of the blade 300 are specifically indicated at 300U and 300L in FIGS. 31 and 32 respectively.

The blades 300 have planes diverging upward (FIG. 17) from the plane of the support 301 (i.e. from the corresponding diametral plane of the funnel 30 indicated by the right hand half of the cutting line 31-31 of FIG. 30 and constituting the plane of the page in FIGS. 31 and 32). The left hand portion of the cutting line 31—31 in FIG. 30 proceeds along the lower outer edge 316 of the left blade 300 in FIGS. 30–32. Accordingly, it will be seen in FIG. 31 that the blade 300 in its upper position 300U locates the convex lower outer edge 316 thereof with its upper end portion 316U substantially in contact with the frustoconical wall 31 of the funnel 30 and its lower portion 316L, spaced radially inboard from the frustoconical wall 31 of the funnel 30. Thus, the convex lower outer blade edge 316 and the adjacent portion of the frustoconical wall 31 diverge downwardly from each other to open a slim tapered space 324 therebetween as seen in FIG. 31. In its upper position 300U of FIG. 31, the blade 300 has its outer transition 317 spaced just below the cylindrical top portion 41 of the funnel 30, the upper outer blade edge 322 curving upward and radially inward away from such cylindrical portion 41 and the blade top edge 323 being spaced between the top and bottom of such cylindrical portion 41, and hence being spaced from the lid 45 and the frustoconical portion 31, of the funnel 30. In this position, any cement material being mixed, which may tend to climb the frustoconical wall 31, is forcibly scraped or wiped therefrom if it rises up near the narrow upper closed end of the space 324, adjacent the blade upper edge portion 316U. The space 324 between the lower portion 316L of the outer blade edge 316 and the frustoconical wall 31 allows relatively low friction between the blade and frustoconical wall so that during early stages of mixing, the shaft assembly can be rotated both clockwise and counterclockwise (such that the blades 300 move with either their upward angled face leading or trailing rotationally). Thus, in its upper, FIG. 31 position, the shaft 271 and blades 300 will normally be rotated in both rotational directions, so that the outer edge 316 thereof either leads (in a scraping manner) to force cement up the frustoconical wall, or trails (in a wiping manner) to force cement down the wall, according to the wishes of the user, to give the best and most rapid mixing.

In the lower, FIG. 32 position of the blades and shaft, each outer lower blade edge portion 316 has substantially its entire length in contact with the frustoconical wall 31 of the funnel 30. Rotation in this position will normally be in the wiping, rather than scraping, direction, with the outer edge 316 of the blade trailing (clockwise movement in FIG. 30). In this rotational direction, the top edge 323 of the blade circumferentially leads the bottom portion 305, 316L thereof, as seen in FIG. 30, to effectively wedge mixed cement downward toward the bottom of the funnel and the piston 140. In the lower, FIG. 32 position of the shaft and blades the extreme lower portions 316EL of the blade outer edges 316, which indeed define outer edge portions of the support 301 of the blade unit, bottom on the frustoconical wall 31 of the funnel 30 and help pilot the rotating shaft 271 substantially coaxially within the funnel and assure that both blade outer edges 316 bear evenly on the frustoconical wall 31 of the funnel for maximum cleaning of mixed cement therefrom and maximum delivery of mixed cement downwardly onto the piston 140 and cartridge 12.

In the upper position of the shaft (FIG. 31), the bottom of the shaft 271, snugly containing the depending tongue 310 of the blade unit, pilots in the upward opening depression 142 in the upper piston 140 to further help maintain substantial coaxiality of the shaft assembly 54 with respect to the funnel 30. However, in the lower shaft position, the piston 140 has fallen into the cartridge, and piloting of the shaft is by the outer edge portions of the support 301 on the bottom portion of the frustoconical wall 31.

In the upper (FIG. 31) position of the shaft assembly 54, both O-rings 280 and 281 thereof maintain sealing contact with the hub 52 of the lid 45. Even in the lower (FIG. 32) position of the shaft assembly 54, at least the upper O-ring 280 maintains sealing engagement with the lid hub 52. This avoids air leakage into the funnel 30 through the lid hub 52 when the funnel 30 is subatmospheric pressure, despite the vertical positioning of the shaft assembly 54.

FIGS. 31A and 32A are enlargements of portions of respective FIGS. 31 and 32 and more clearly show the

15 downward displacement of the piston 140 in response to lowering of the shaft assembly from its FIG. 31 upper position to its FIG. 32 lower position, and hence, the corresponding displacement from upper portion 301U to lower position 301L of the support 301. Thus, the piston 140 is firmly yet resiliently supported in its upper position by 140U in FIG. 31A by reception of the bead 150 of the funnel 30 in the annular detent groove 151 of the piston. Downward movement of the rotatable shaft 271 from its FIG. 31 to its FIG. 32 position causes its lower end to push the piston downward, unseating the resilient connection between the bead 150 and groove 151, and driving the piston down below the bead 150 and entirely into the upper end of the cartridge 12, as seen in FIGS. 32 and 32A.

As a result of being packed in the bottom of the funnel, the lip seal 146 (FIG. 7) takes a slight radially inward set. As it is kicked down by the shaft after mixing, and it falls down into the cartridge 12, that set begins to relax outwardly. By the time the cartridge 12 is filled, the lip seal 146 is substantially fully relaxed.

Piston 140 tends to float easily down in the cartridge 12, and not stick part way down into it, because (1) of the "set" in the lip seal 146, (2) the cartridge diameter is slightly larger (e.g. by about 0.025 inch) than the funnel outlet diameter, and (3) of gravity acting on the weight of the piston 140 and cement mass above it.

If desired, an opening 306 may be provided in one or each blade 300 as indicated in broken lines in FIG. 18, for example, the opening being located above, or extending below, the normal liquid level in the funnel, which is approximately at the height of the point 320 on the inner edge of the blade.

Operation

The operation of the apparatus 10 has been discussed in detail above but will be briefly summarized here for convenient reference.

Figure 1C:
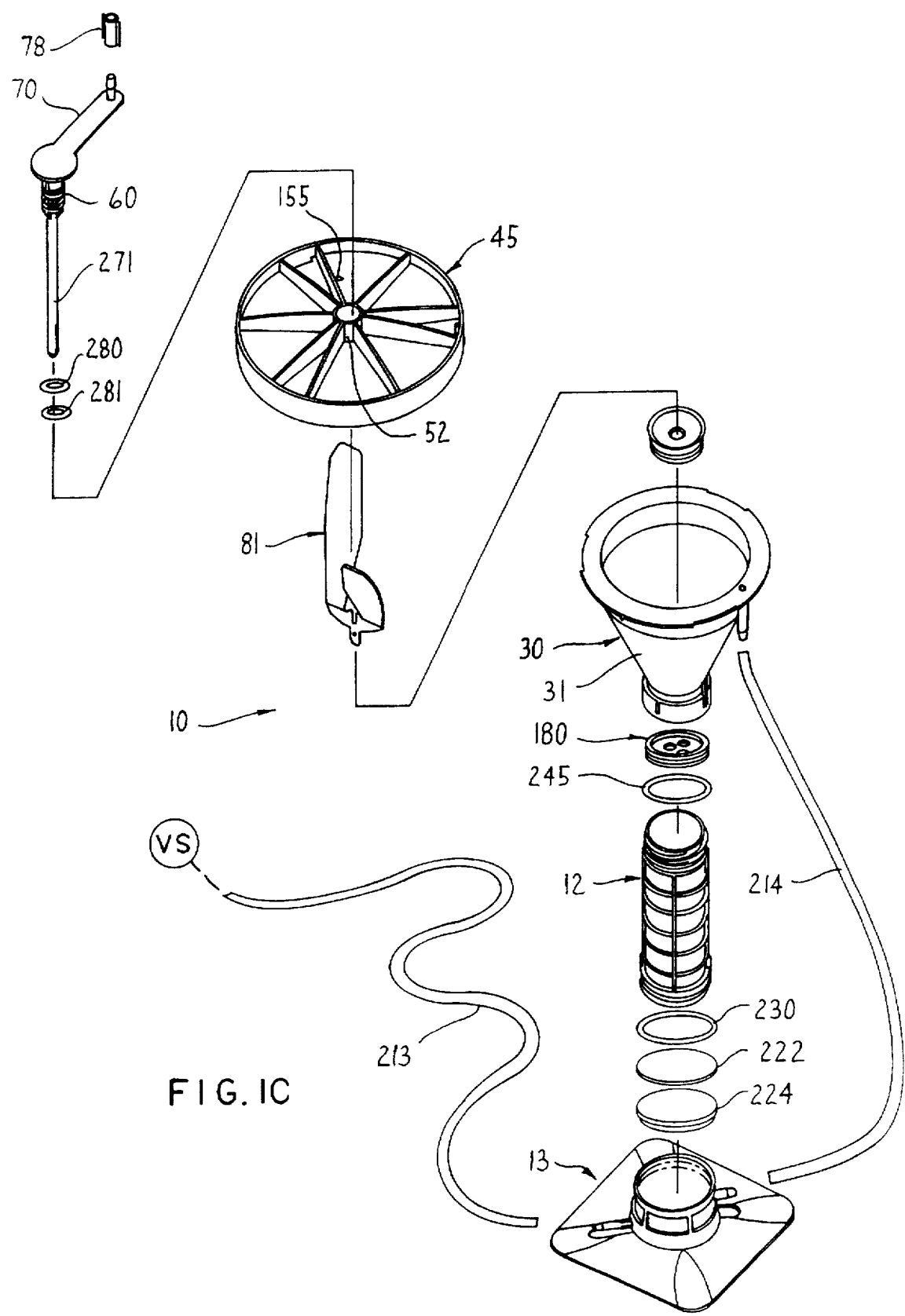
FIG. 1C is an exploded pictorial view of the FIG. 1 apparatus.

The apparatus is conveniently assembled as follows. The O-rings 280 and 281 (FIG. 1C) are slid onto the shaft 271 and into their grooves in the body 60 and the shaft is slid downward through open hub 52 of the lid 45. The blade unit 81 is snap fitted into the bottom of the shaft 271. The spinner knob 78, if used, is placed on the handle 70. The adhesive tape vacuum seal AT (FIG. 1) covers the hole 155 in the lid 45. The upper piston 140 is settled in the bottom of the funnel 30 (FIG. 1C). The lid 45, with its underlying seal ring 256 (FIG. 31), is then twisted onto its fixed, sealing position atop the funnel 30, leaving the shaft 271 and blade unit 81 within the funnel 30, with the bottom of the shaft 271 engaging the upper piston 140 and the parts positioned as shown in FIG. 31. The lower piston 180 is inserted downward into the cartridge 12. The cartridge 12, with its O-rings 245 and 230 installed thereon, is threaded into the bottom of the funnel 30. The base 13, with the filter disk 222 and filter puck 224 installed therein, is pushed on to the bottom end of the cartridge 12, as seen in FIGS. 1C and 2. The tubes 213 and 214 are connected to the base 13 and the tube 214 is also connected to the funnel 30.

The completed apparatus 10 is packaged in a sterile manner for shipment and future use.

In use, normally in a surgical operating room, a surgical assistant (e.g. nurse) unthreads the lid 45 from the top of the funnel 30 and pours cement components (typically a liquid and powder) into the open top of the funnel. Such materials settle toward the bottom of the funnel and onto the top of the upper piston 140. The lid 45 is then screwed back onto the top of the funnel 30 and the vacuum source VS connected to vacuum tube 213 is turned on to apply subatmospheric pressure to the base 13 and to the funnel 30 and cartridge 12 on both sides of the upper piston 140. The parts are then in their FIG. 31 position.

During mixing, the apparatus may rest with its base atop a table or surgical cart while the user (e.g. nurse) rotates the crank handle 70. However, the apparatus is light enough and the cartridge 12 and bottom portion of the funnel 30 provide a convenient enough handgrip that the nurse may prefer to hold the apparatus by his/her waist with one hand and turn the crank handle 70 with the other, particularly in that the mixing process can be continuously watched through the transparent lid 45.

During initial mixing the user may alternatively rotate the crank handle 70 in both rotational directions to alternate the rotational direction of the blade unit 81. The downward divergence of the blades 300 and funnel frustoconical wall 31 (leaving the upwardly narrowing space 324 in FIG. 31) has been found to help the blades, as they rotate during mixing, push cement components upwardly, leaving a upward tapering coating of cement mixture on the walls, where the blades can more effectively squish voids and air bubbles out of the mixture. This is unlike in systems with a constant separation distance between radially outer blade edge and mixing bowl wall, wherein the cement components to be mixed tend to stay in a lump at the bottom of the bowl, where much of the radially outer blade edge cannot reach same to squeeze voids and air bubbles therefrom.

The upward tapering space 324 also means that the upper blade edge portion 316U is strongly resiliently urged against the funnel peripheral wall 31, as the shaft 217 and blade unit are pushed downward with the handle 70 by the user, to push cement from the funnel down into the cartridge 12. This is despite the tendency of cement on the inside of the frustoconical wall 31 to resiliently bend the upper ends of the blades back and away from the wall 31. Thus, there is less of a tendency to leave mixed bone cement on the upper portion of the inner surface of the funnel 30 after completion of mixing and loading, than tends to be the case with a constant separation between blade edge and mixing bowl wall as in the prior art.

In its lowered FIG. 32 position, rotation of the blade unit 81 in a direction with the tops of the blades rotationally leading and the lower outer edge 316 of the blades trailing, it will be seen that blades tend to wipe the frustoconical wall 31 circumferentially and press down the syrupy mixed cement downward into the bottom of the funnel 30. During this wiping of mixed cement from the walls of the funnel down into the cartridge, the support 301 of the blade unit 81 uses the bottom of the funnel as a radial thrust bearing, to help maintain firm pressure of the blade edges continuously and consistently along the frustoconical wall surface of the portion 31 of the funnel 30.

As the handle assembly 54 is displaced downward, the lower end of the shaft 271 snaps the upper piston 140 down out of its resilient detent engagement with bead 150 and displaces it downward entirely into the top of the cartridge 12, to allow mixed cement to fill the cartridge and act with gravity to force the top piston 140 downward in the cartridge 12.

Following loading of the cartridge 12, the upper piston 140 seats upon the lower piston 180 at the bottom of the cartridge and is in turn overfilled with mixed cement. At this point, the tape AT is lifted, exposing the lid hole 155 and, venting the apparatus to atmospheric pressure. The cartridge 12 can then be lifted from the base 13 and unscrewed from the bottom of the funnel 30, be provided with a tip (as above mentioned) at a separate end and be placed in a dispensing gun (as above mentioned) for inserting bone cement under pressure into the surgical site on a patient.

The used funnel 30 can then be placed bottom downward in the upstanding cup of the base 13 and left there during the remaining of the surgical procedure and thereafter be disposed of.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A hard tissue repair cement mixer apparatus, comprising:
    a mixing chamber having a conical, upward diverging inner surface, a length axis, and an inlet for receiving cement components to be mixed;
    a blade rotatably supported for rotation about the length axis of said conical mixing chamber, said blade having a radially outer edge upwardly converging into contact with an upper portion of said conical mixing chamber, said blade angling divergently upward from a plane containing said axis,
    whereby rotation of said blade tends to force cement radially outward toward and up said conical inner surface of said mixing chamber in an upwardly thinning layer and therewith expedite release of trapped gas in the cement mix.

2. The apparatus of claim 1 in which said blade has an upper end and a bottom end, said blade in said upper cement mixing position contacting said mixing chamber wall adjacent said upper end of said blade and being spaced further from said mixing chamber wall adjacent said bottom end of said blade.

3. The apparatus of claim 1 including a blade unit of substantially rigid material and comprising a central support having an upstanding central rotation axis and two substantially symmetrical ones of said blades upstanding from said central support on opposite sides of said central rotation axis, said blades being bent in opposite directions from the plane of said central support substantially along a line defining the top edge of said support.

4. The apparatus of claim 1 including a window in said blade.

5. A hard tissue repair cement mixer apparatus, comprising:
    a mixing chamber having a wall, a length axis and an inlet for receiving cement components;
    a blade rotatable supported on the length axis of said mixing chamber, said blade having an outer edge, said blade having an axial position in said chamber in which there is an upwardly convergent space between an outer edge of said blade and a wall of said mixing chamber;
    said blade having an upper end and a bottom end and a first axial position in which it is at least close to said mixing chamber wall adjacent said upper end of said blade and is spaced further from said mixing chamber wall adjacent said bottom end of said blade in which said blade is of resiliently bendable material and has a radially outer edge, in which substantially the entirety of said radially outer edge of said blade is bent into engagement with said mixing chamber wall, in said lower shaft position, for wiping cement from said wall and driving it toward said narrower lower portion of said mixing chamber, said chamber having an outlet at said narrowed lower portion.

6. A hard tissue repair cement mixer apparatus, comprising:
    a mixing chamber having a wall, a length axis and an inlet for receiving cement components;
    a blade rotatable supported on the length axis of said mixing chamber, said blade having an outer edge, said blade having an axial position in said chamber in which there is an upwardly convergent space between an outer edge of said blade and a wall of said mixing chamber;
    said blade having an upper end and a bottom end and a first axial position in which it is at least close to said mixing chamber wall adjacent said upper end of said blade and is spaced further from said mixing chamber wall adjacent said bottom end of said blade in which said mixing chamber has a frustoconical portion, said blade having a convexly rounded radially outer edge and being bent away from a first plane containing the length axis and a diameter of said frustoconical mixing chamber portion so as to diverge upward therefrom, said blade lying in a second plane diverging from said first plane add intersecting the frustoconical wall of said mixing chamber along a curved line.

7. A hard tissue repair cement mixer apparatus, comprising:
    a mixing chamber having a wall, a length axis and an inlet for receiving cement components;
    a blade rotatable supported on the length axis of said mixing chamber, said blade having an outer edge, said blade having an axial position in said chamber in which there is an upwardly convergent space between an outer edge of said blade and a wall of said mixing chamber;
    a blade unit of substantially rigid material and comprising a central support, said blade being upstanding from said support, said blade unit having diametrally opposite edges adjacent the join of said support and blade and conforming substantially to the shape of said mixing chamber and bearing thereon such that said mixing chamber defines a radial thrust bearing for said blade unit, in a second axial position of said blade.

8. A hard tissue repair cement mixer apparatus, comprising:
    a frustoconical mixing chamber having a narrow outlet end portion;
    a piston resiliently snap fitted in said narrow outlet end portion of said frustoconical mixing chamber;
    a blade/shaft assembly including a shaft and a blade fixed on said shaft, said blade/shaft assembly being supported for rotation in said mixing chamber and being axially displaceable in said mixing chamber toward said narrow end of said mixing chamber, said blade/shaft assembly having a bottom end and a mixing position in which said bottom end is axially supported on said piston to prevent unintended axial displacement of said blade/shaft assembly further toward said narrow end portion of said mixing chamber during initial mixing of cement.

9. The apparatus of claim 8 including a lid on said mixing chamber axially remote from said narrow end portion thereof, said shaft extending sealingly and rotatably through said lid at a location axially remote from said narrow mixing chamber end portion, said piston locating the axial mixing position of said blade independent of stacking of tolerances in said mixing chamber, lid and shaft.

10. The apparatus of claim 9 in which said piston has a central depression receiving an end of said shaft to pilot same radially of said mixing chamber.

11. The apparatus of claim 9 wherein, with the apparatus assembled for shipping, said blade/shaft assembly has a shipping position in which said assembly is elevated in said mixing chamber out of contact with said piston, thereby allowing removal of said lid and shaft from said mixing chamber, addition of cement components to be mixed into the thus opened end of said mixing chamber and reapplication of said lid and shaft assembly to said mixing chamber without risk of accidentally having the lower shaft end drive said piston out of said mixing chamber.

12. The apparatus of claim 9 including means for applying a subatmospheric pressure to said mixing chamber and therewith for displacing said shaft axially inward of said mixing chamber into contact with said piston during initial rotation of said shaft for mixing.

13. The apparatus of claim 8 including a lid on said mixing chamber axially remote from said piston and having an upstanding hub, said shaft extending sealingly and rotatably through said hub, said shaft having a pair of axially spaced seal rings, at least one of which seal rings sealingly engages said hub regardless of the axial operating position of said shaft with respect to said hub.

14. A hard tissue repair cement mixer apparatus, comprising:
a conical mixing chamber having a narrow outlet end portion;
a piston resiliently snap fitted in said narrow outlet end portion of said frustoconical mixing chamber;
a blade/shaft assembly supported for rotation in said mixing chamber and being axially displaceable in said mixing chamber toward said narrow end of said mixing chamber;
a cartridge removably fixed at said narrow outlet end portion of said mixing chamber;
a vacuum seal ring radially between said mixing chamber outlet end portion and the adjacent end of said cartridge to enable maintenance of subatmospheric pressure at least on the cartridge side of said piston.

15. The apparatus of claim 14 including a detent resiliently fixing said piston adjacent the join of said mixing chamber outlet end portion and said cartridge, said shaft having a hand actuable means outside of said mixing chamber for rotating said shaft to mix cement and for axially advancing said shaft and therewith pushing said piston out of engagement with said detent and into said cartridge to enable loading mixed cement into said cartridge.

16. The apparatus of claim 8 in which said blade/shaft assembly includes a support fixed to said shaft adjacent the bottom thereof, said blade extending up from said support, said support axially opposing said narrow outlet end portion of said mixing chamber and having a portion shiftable down into contact with said narrow outlet end portion of said mixing chamber for positively stopping axial advance of said shaft along the narrowing direction of said mixing chamber.

17. A hard tissue repair cement mixer apparatus, comprising:
a conical mixing chamber having a narrow outlet end portion;
a piston resiliently snap fitted in said narrow outlet end portion of said frustoconical mixing chamber;
a blade/shaft assembly supported for rotation in said mixing chamber, and being axially displaceable in said mixing chamber toward said narrow end of said mixing chamber said blade/shaft assembly unit including a support and means fixed to the bottom end portion of said shaft near said piston, an end slot in said shaft end portion open toward said piston and of thickness to snugly slidably receive the central part of said support, said shaft having a web extending axially into said slot part way to the open end of said slot, said support having a central notch open toward and snugly receiving said web to prevent rocking of said support in its own plane within said shaft slot, a hole in said support spaced axially from said notch and a tooth on said shaft extending partly into said slot at a point axially spaced from said web, said tooth being sized for snug reception in said hole in said support to positively lock said support on said shaft, said support including a tongue extending away from said hole and toward said piston substantially to the end of said shaft slot.

18. A hard tissue repair cement mixer apparatus, comprising:
a base having first and second vacuum ports, said first port being connectable to a vacuum source;
a cartridge removably upstanding on said base for receiving mixed cement, said cartridge having a bottom portion communicating with said base;
a mixing chamber removably upstanding on said cartridge for mixing cement and loading said cartridge with mixed cement, said mixing chamber having a third vacuum port.

19. The apparatus of claim 18 including a flexible tube connecting said second and third vacuum ports and applying the same subatmospheric pressure in said base to said mixing chamber and said cartridge, said tubing being longer than the distance between said second and third ports to allow removal of said cartridge from between said base and mixing chamber.

20. The apparatus of claim 18 including filter means in said base and operatively interposed between (1) said first port and (2) said cartridge and second port.

21. The apparatus of claim 20 in which said base has an upward opening cup, said filter means being in said cup with said first port below same and said cartridge and second port above said filter means.

22. The apparatus of claim 21 in which said filter means comprises a substantially rigid porous disk-like element supported on a step in said base, said base having a chamber below said filter disk element and connected with said first port, said base having a chamber above said filter disk element and receiving the bottom of said cartridge therein.

23. The apparatus of claim 22 in which said filter element comprises a porous disk-like puck of polyethylene and activated charcoal.

24. The apparatus of claim 23 including two filter elements one atop the other between said chambers and including a porous polyethylene disk atop said puck.

25. The apparatus of claim 21 including a transparent lid on said mixing chamber for user viewing of cement mixing progress, wherein for presenting a clean appearance, said mixing chamber and cartridge and base are of light colored rigid plastics material and said filter means comprises a porous activated charcoal filter element covered by a porous filter disk of light colored material such that said charcoal filter is not visible by the user.

26. The apparatus of claim 18 in which said cartridge has top and bottom O-rings snugly and vacuum sealingly received in said mixing chamber outlet and said base cup, respectively, for effective vacuum tight connection between said base and mixing chamber, means for applying a subatmospheric pressure to both ends of the join of the said cartridge to said mixing chamber and comprising a tube connecting said second and third vacuum ports.

27. The apparatus of claim 18 including circumferentially spaced axial ribs on the bottom portion of said cartridge to help it stand firmly upright in said cup.

28. The apparatus of claim 18 including circumferentially spaced axial ribs on the outlet portion of said mixing chamber to help said mixing chamber stand firmly upright in said cup, after filling of the cartridge with mixed cement and removal of the filled cartridge for dispensing cement to the patient, and prior to disposal of said mixing chamber and base.

29. The apparatus of claim 18 in which the bottom of said mixing chamber is similarly sized to that of said cartridge to alternatively fit on and be supported by said base after filling and removal of said cartridge from said base and mixing chamber, filter means on said base between said first vacuum port and the alternatively fitted one of said mixing chamber and cartridge, a flexible vacuum tube connecting said second and third vacuum ports all for maintaining closure of said mixing chamber and base against significant leakage of cement vapor therefrom except through said filter means on said base and so as to suppress escape of such cement vapor to the atmosphere surrounding the apparatus.

30. The apparatus of claim 18 in which said base includes shock absorbing means for allowing the user to tap the apparatus on a supporting table, as to shakedown cement powder in said mixing chamber, said shock absorbing means comprising a shallow, substantially frustoconical foot, downwardly concave in its center and with a downwardly diverging wall of sufficient thinness and flexibility to absorb a portion of upward directed mechanical shocks by flexing.

31. The apparatus of claim 18 in which said mixing chamber and cartridge and base are all of molded plastics material, to make the apparatus entirely disposable after a single use and to avoid the need for cleaning and resterilization and to avoid cross-patient contamination.

32. A hard tissue repair cement mixer apparatus, comprising:
    an upstanding cartridge having an upper end for receiving mixed cement and a bottom portion connectable to a vacuum source;
    a mixing chamber removably supported on and upstanding from the upper end of said cartridge for mixing cement and having a bottom outlet for loading said cartridge with mixed cement, said mixing chamber having a vacuum port connectable to a vacuum source, said cartridge having an elongate tubular peripheral wall defined by a cement engaging interior surface and an exterior surface open to the atmosphere, said cartridge peripheral wall being capable of sustaining a pressure drop radially thereacross from outside atmospheric pressure to a subatmospheric pressure corresponding to connection of said bottom portion to a vacuum source.

33. The apparatus of claim 32 including a piston in said cartridge adjacent said chamber, in which said chamber has an outlet and said cartridge has an inlet telescoped with respect to said outlet, a vacuum seal ring radially between said mixing chamber outlet and said cartridge inlet to enable maintenance of subatmospheric pressure at least on the cartridge side of said piston.

34. A hard tissue repair cement mixer apparatus, comprising:
    a cement mixing-chamber having a downward tapered inner surface and an inlet for receiving cement components, a wider upper portion and a narrower lower portion;
    an upstanding shaft and structure in said mixing chamber supporting said shaft for displacement between an upper position therein and a lower position therein;
    a blade fixed on said shaft and movable with said shaft downward along said downward tapered mixing chamber inner surface from an upper cement mixing position at said wider upper portion of said mixing chamber to a lower mixed cement scraping and outputting position at said narrower lower portion of said mixing chamber.

35. The apparatus of claim 34 in which said narrower lower portion of said mixing chamber includes a narrow outlet end portion and a piston resiliently snap fitted in said narrow outlet end portion, said shaft being of length to push said piston out of said outlet in response to dropping of said blade into said lower mixed cement scraping and outputting position.

36. The apparatus of claim 35 including an upward tapering gap between said blade and said mixing chamber inner surface in said upper position of said blade, said gap being absent in said lower position of said blade.

37. The apparatus of claim 35 in which the bottom of said shaft engages said piston aand is displaceable downward sufficient to dislodge the piston from said mixing chamber.

38. The apparatus of claim 35 in which said shaft and blade define a unitary shaft/blade assembly having a bottom end piloted in said piston.

39. The apparatus of claim 34 including means for maintaining a subatmospheric pressure in said vacuum chamber in both said upper and lower positions of said shaft, so as to permit movement of said shaft from said upper to lower position, said mixing chamber having a closure at the top thereof, said shaft having an upper part extending slidably through said closure, and first and second annular seals disposed radially between said closure and shaft to avoid leakage of atmosphere past said closure and shaft into said mixing chamber, said annular seals being axially separated sufficient to maintain at least one said annular seal interposed between said shaft and closure throughout the range of axial movement of said shaft.

* * * * *

UNITED STATES PATENT AND TRADEMARK OFFICE
CERTIFICATE OF CORRECTION

PATENT NO. : 5,797,679
DATED : August 25, 1998
INVENTOR(S) : David H. GRULKE, et al.

It is certified that error appears in the above-identified patent and that said Letters Patent is hereby corrected as shown below:

Column 17, line 53; after "components"
    insert ---and a narrower lower portion---.
  line 54; replace "rotatable"
    with ---rotatably---.
  line 58; replace "a" with ---said---.
  line 63; after "blade" insert ---,---.
  line 67; replace "said" (second occurrence)
    with ---a---.

Column 18, line 1; replace "shaft" with ---axial---.
  line 9; replace "rotatable"
    with ---rotatably---.
  line 12; replace "an" (second occurrence)
    with ---the---.
  line 13; delete "a"., insert -- said --.
  line 24; replace "add" with ---and---.
  line 30; replace "rotatable"
    with ---rotatably---.
  line 34; replace "an" (second occurrence)
    with ---the---.
  line 35; replace "a" with ---said---.

UNITED STATES PATENT AND TRADEMARK OFFICE
CERTIFICATE OF CORRECTION

PATENT NO. : 5 797 679
DATED : August 25, 1998
INVENTOR(S) : David H. GRULKE, et al.

It is certified that error appears in the above-identified patent and that said Letters Patent is hereby corrected as shown below:

Column 19, line 45; after "cartridge,"
    insert ---said blade/shaft assembly
    including a shaft,---.
Column 20, line 2; after "chamber" insert ---,---.
    line 66; after "in" insert ---an outlet of---.
        after "and" insert ---in---.
    delete "cup"
Column 21, line 7; replace "cup" with ---base---.
    line 11; replace "cup" with ---base---.
Column 22, line 2; delete "said chamber has".
    line 3; delete "an outlet and".
    line 10; replace "mixing-chamber" with
    ---mixing chamber---.
    line 37; replace "aand" with ---and---.

Signed and Sealed this

Fifth Day of December, 2000

Attest:

Q. TODD DICKINSON

*Attesting Officer*     *Director of Patents and Trademarks*